(12) United States Patent
Bekkaoui et al.

(10) Patent No.: US 6,503,709 B1
(45) Date of Patent: *Jan. 7, 2003

(54) METHODS FOR RAPIDLY DETECTING METHICILLIN RESISTANT STAPHYLOCOCCI

(75) Inventors: Faouzi Bekkaoui, Burnaby; Lynn P. Cloney, Vancouver, both of (CA)

(73) Assignee: ID Biomedical Corporation, Bothell, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/109,329

(22) Filed: Jul. 2, 1998

Related U.S. Application Data

(60) Provisional application No. 60/090,276, filed on Jun. 22, 1998, provisional application No. 60/086,020, filed on May 18, 1998, and provisional application No. 60/051,643, filed on Jul. 3, 1997.

(51) Int. Cl.$^7$ ............................ C12Q 1/68; C07H 21/04
(52) U.S. Cl. ...................... 435/6; 435/24.33; 536/24.3; 536/24.32; 536/23.1
(58) Field of Search ............................ 536/24.3, 24.32, 536/23.1; 435/6, 24.33

(56) References Cited

U.S. PATENT DOCUMENTS

| | | | |
|---|---|---|---|
| 4,257,774 A | 3/1981 | Richardson et al. ...... 23/230 B |
| 4,876,187 A | 10/1989 | Duck et al. .................... 435/6 |
| 5,011,769 A | 4/1991 | Duck et al. .................... 435/6 |
| 5,367,066 A | 11/1994 | Urdea et al. ............... 536/24.3 |
| 5,403,711 A | * 4/1995 | Walder et al. ................. 435/6 |
| 5,491,063 A | 2/1996 | Fisher et al. .................. 435/6 |
| 5,573,907 A | 11/1996 | Carrino et al. ................. 435/6 |
| 5,641,633 A | 6/1997 | Linn et al. ..................... 435/6 |
| 5,660,988 A | 8/1997 | Duck et al. .................... 435/6 |
| 5,731,146 A | 3/1998 | Duck et al. .................... 435/6 |
| 5,759,811 A | 6/1998 | Epstein et al. ............. 435/69.1 |
| 5,770,361 A | 6/1998 | Arthur et al. .................. 435/6 |
| 5,824,518 A | 10/1998 | Kacian et al. ........... 435/91.21 |

FOREIGN PATENT DOCUMENTS

| | | |
|---|---|---|
| DE | 43 38 119 A1 | 5/1995 |
| EP | 227 976 | 7/1987 |
| EP | 229 442 | 7/1987 |
| EP | 229 701 | 7/1987 |
| EP | 382 433 | 8/1990 |
| EP | 497 272 | 8/1992 |
| EP | 500 224 | 8/1992 |
| EP | 527 628 | 2/1993 |
| EP | 578 138 | 1/1994 |
| EP | 713 921 | 5/1996 |
| FR | 2 699 537 A1 | 6/1994 |
| JP | 08 252099 | 10/1996 |
| WO | WO 88/05538 | 7/1988 |
| WO | WO 92/18649 | 10/1992 |
| WO | WO 92/18650 | 10/1992 |
| WO | WO 93/01311 | 1/1993 |
| WO | WO 93/15226 | 8/1993 |
| WO | WO 93/20233 | 10/1993 |
| WO | WO 94/12665 | 6/1994 |
| WO | WO 95/00667 | 1/1995 |
| WO | WO 95/05480 | 2/1995 |
| WO | WO 95/14106 | 5/1995 |
| WO | WO 96/08582 | 3/1996 |
| WO | WO 96/20287 | 7/1996 |
| WO | WO 97/11199 | 3/1997 |
| WO | WO 97/43450 | 11/1997 |

OTHER PUBLICATIONS

Stratagene Catalog. 1998. p. 39.*
Lencastre et al. Antimicrobial agents and chemotherapy, 35(4), pp. 632–639, Apr. 1991.*
Ryffel et al. Gene. 94, pp. 137–138, 1990.*
Archer et al. Antimicrobial agents and chemotherapy. 34(9), pp. 1720–1724, Aug. 1990.*
Song et al. FEBS Letters. 221(1), pp. 167–171, Aug. 1987.*
Al–Obeid et al., "Comparison of vancomycin–inducible proteins from four strains of Enterococci," *FEMS Microbiology Letters 70:* 101–106, 1990.
Altwegg, "General problems associated with diagnostic applications of amplification methods," *Journal of Microbiological Methods 23:* 21–30, 1995.
Arthur et al., "The vanZ gene of Tn1546 from *Enterococcus faecium* BM4147 confers resistance to teicoplanin," *Gene 154:* 87–92, 1995.
Baker et al., Database EMBL, ID/Accession No. V36396, May 22, 1998.

(List continued on next page.)

*Primary Examiner*—W. Gary Jones
*Assistant Examiner*—Juliet Einsmann
(74) *Attorney, Agent, or Firm*—Seed IP Law Group PLLC

(57) ABSTRACT

Compositions and methods are provided for determining the presence of an antibiotic resistant mecA gene in a biological sample, comprising the general steps of (a) treating cells contained within a biological sample to expose target single-stranded nucleic acid molecules; (b) reacting the target single-stranded nucleic acids with a scissile link-containing nucleic acid which is complementary to a portion of an antibiotic resistant mecA gene, and with an enzyme which cleaves double-stranded target-probe complexes, under conditions which allow the target and probe to hybridize to each other to form a double-stranded target-probe complex, the enzyme molecule being capable of cleaving the scissile link of the target-probe complex such that one or more fragments of the nucleic acid probe released from said complex; and (c) determining whether cleaved portions of the detecting probe fragments released from said nucleic acid probe are produced, and thereby detecting the presence of the antibiotic resistant mecA gene.

23 Claims, 10 Drawing Sheets

OTHER PUBLICATIONS

Beggs et al., "Characterization of *Mycobacterium Tuberculosis* Complex Direct Repeat Sequence for Use in Cycling Probe Reaction," *Journal of Clinical Microbiology* 34(12): 2985–2989, 1996.

Bekkaoui et al., "Cycling Probe Technology with RNase H Attached to an Oligonucleotide," *BioTechniques* 20:240–248, 1996.

Brisson–Noël et al., "Cloning and Heterospecific Expression of the Resistance Determinant vanA Encoding High–Level Resistance to Glycopeptides in *Enterococcus faecium* BM4147," *Antimicrobial Agents And Chemotherapy* 34(5): 924–927, 1990.

Bugg et al., "Identification of Vancomycin Resistance Protein VanA as a D–Alanine:D–Alanine Ligase of Altered Substrate Specificity," *Biochemistry* 30: 2017–2021, 1991.

Carey, "Gel Retardation at Low pH Resolves trp Repressor–DNA Complexes for Quantitative Study," *Proc. Natl. Acad. Sci. USA* 85:975–979, 1988.

Carrino and Lee, "Nucleic acid amplification methods," *Journal of Microbiological Methods* 23: 3–20, 1995.

Cloney et al., "Rapid Detection of the mecA Gene in Clinical Isolates Using a Novel DNA–Probe Assay," *Abstracts of the General Meeting of the American Society for Microbiology* 97(4–8): p. 171, abstract No. C–292, 1997.

Devlin et al., "Homogeneous Detection of Nucleic Acids by Transient–State Polarized Fluorescence," *Clin. Chem.* 39(9):1939–1943, 1993.

Duck et al., "Probe Amplifier System Based on Chimeric Cycling Oligonucleotides," *BioTechniques* 9(2): 142–147, 1990.

Dutka–Malen et al., "Phenotypic and Genotypic Heterogeneity of Glycopeptide Resistance Determinants in Gram–Positive Bacteria," *Antimicrobial Agents And Chemotherapy* 34(10): 1875–1879, 1990.

Dutka–Malen et al., "Sequence of the vanC gene of *Enterococcus gallinarum* BM4174 encoding a D–alanine:D–alanine ligase–related protein necessary for vancomycin resistance," *Gene* 112: 53–58, 1992.

Dutka–Malen et al., "The VANA glycopeptide resistance protein is related to D–alanyl–D–alanine ligase cell wall biosynthesis enzymes," *Mol. Gen. Genet.* 224: 364–372, 1990.

Evers et al., "The vanB gene of vancomycin–resistant *Enterococcus faecalis* V583 is structurally related to genes encoding D–Ala:D–Ala ligases and glycopeptide–resistance proteins VanA and VanC," *Gene* 124: 143–144, 1993.

Fuller et al., "Rapid Detection of Methicillin Resistant *Staphylococcus Aureus* (MRSA) Using Cycling Probe Technology (CPT)," *Abstracts of the General Meeting of the American Society for Microbiology* 98, p. 199, abstract No. C–408, 1998.

Germann and Telenti, "Nucleic acid amplification methods in diagnostic virology," *Journal of Microbiological Methods* 23: 31–39, 1995.

Gibson et al., "A Homogeneous Method for Genotyping with Fluorescence Polarization," *Clin. Chem.* 43(8):1336–1341, 1997.

Hebenbrock et al., "Single Strand Conformational Polymorphism Using Capillary Electrophoresis with Two–Dye Laser–Induced Fluorescence Detection," *Electrophoresis* 16:1429–1436, 1995.

Heyduk et al., "Fluorescence Anisotropy: Rapid, Quantitative Assay for Protein–DNA and Protein–Protein Interaction," *Methods in Enzymology* 274:493–503, 1996.

Kitchin et al., "Avoidance of false positives," *Nature* 344: p. 201, 1990.

Kumke et al., "Hybridization of Fluorescein–Labeled DNA Oligomers Detected by Fluorescence Anisotropy with Protein Binding Enhancement," *Anal. Chem.* 67:3945–3951, 1995.

Kwok and Higuchi, "Avoiding false positives with PCR," *Nature* 339: 237–238, 1989.

Leclercq et al., "Transferable Vancomycin and Teicoplanin Resistance in *Enterococcus faecium*," *Antimicrobial Agents And Chemotherapy* 33(1): 10–15, 1989.

Lundblad et al., "Fluorescence Polarization Analysis of Protein–DNA and Protein–Protein Interactions," *Molecular Endocrinology* 10(6):607–612, 1996.

Modrusan et al., "Spermine–mediated improvement of cycling probe reaction," *Molecular and Cellular Probes* 12: 107–116, 1998.

Murakami et al., "Fluorescent–Labeled Oligonucleotide Probes: Detection of Hybrid Formation in Solution by Fluorescence Polarization Spectroscopy," *Nucleic Acids Research* 19(15):4097–4102, 1991.

Niederhauser et al., "Reliability of PCR Decontamination Systems," *PCR Methods and Applications* 4(2): 117–123, 1994.

Okano and Kambara, "DNA Probe Assay Based on Exonuclease III Digestion of Probes Hybridized on Target DNA," *Analytical Biochemistry* 228:101–108, 1995.

Patel et al., "Multiplex PCR detection of vanA, vanB, vanC–1, and vanC–2/3 Genes in Enterococci," *Journal of Clinical Microbiology* 35(3): 703–707, 1997.

Pingoud et al., "Effect of Polyamines and Basic Proteins on Cleavage of DNA by Restriction Endonucleases," *Biochemistry* 23: 5697–5703, 1984.

Sahm et al., "In Vitro Susceptibility Studies of Vancomycin–Resistant *Enterococcus faecalis*," *Antimicrobial Agents And Chemotherapy* 33(9): 1588–1591, 1989.

Spears et al., "Simultaneous Strand Displacement Amplification and Fluorescence Polarization Detection of *Chlamydia trachomatis* DNA," *Analytical Biochemistry* 247:130–137, 1997.

Walker et al., "Detection of *Mycobacterium tuberculosis* DNA with Thermophilic Strand Displacement Amplification and Fluorescence Polarization," *Clinical Chemistry* 42(10):1604–1608, 1996.

Walker et al., "DNA Detection by Strand Displacement Amplification and Fluorescence Polarization with Signal Enhancement Using a DNA Binding Protein," *Nucleic Acids Research* 24(2):348–353, 1996.

Walker et al., "Strand Displacement Amplification (SDA) and Transient–State Fluorescence Polarization Detection of *Mycobacterium tuberculosis* DNA," *Clinical Chemistry* 42(1):9–13, 1996.

Wetmur, "DNA Probes: Applications of the Principles of Nucleic Acid Hybridization," *Critical Reviews in Biochemistry and Molecular Biology* 26(3/4): 227–259, 1991.

Yao and Kow, "Strand–Specific Cleavage of Mismatch–Containing DNA by Deoxyinosine 3'–Endonuclease from *Escherichia coli*," *J. Biol. Chem.*269(60):31390–31996, 1994.

* cited by examiner

SEQUENCE LISTING

```
<160> NUMBER OF SEQ ID NOS: 26

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 1
aatagagaaa aagaaaaaag atggcaaag                                            29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 2
ctttgccatc tttttctttt ttctctatt                                            29

<210> SEQ ID NO 3
<211> LENGTH: 59
<212> TYPE: RNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 3
cgcacauaca uuaauagaga aaaagaaaaa agauggcaaa gauauucaac uaacuauug       59

<210> SEQ ID NO 4
<211> LENGTH: 89
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 4
gaactttagc atcaatagtt agttgaatat ctttgccatc tttttctttt ttctctatta      60
atgtatgtgc gattgtattg ctattatcg                                            89

<210> SEQ ID NO 5
<211> LENGTH: 29
<212> TYPE: DNA
<213> ORGANISM: Artificial Sequence
```

```
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 5
aatagagaaa aagaaaaaag atggcaaag                                    29

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 6
aatagagaaa aagaaaaaag atggcaaaga aaaaaaaaa aaaaaaa                 47

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 7
aatagagaaa aagaaaaaag atggcaaag                                    29

<210> SEQ ID NO 8
<211> LENGTH: 29
<212> TYPE: RNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 8
aauagagaaa aagaaaaaag auggcaaag                                    29

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 9
tggtaaaaag ggactcgaaa aactt                                        25

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 10
ggtggatagc agtacctgag cc                                           22
```

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Solid
      Phase Synthesis of Nucleic Acid Probe Complementary to
      mecA Gene from Staphylococcal Species

<400> SEQUENCE: 11
agctccaaca tgaagatggc tatcgtgtc                                29

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Solid
      Phase Synthesis of Nucleic Acid Probe Complementary to
      mecA Gene from Staphylococcal Species

<400> SEQUENCE: 12
acctgtttga gggtggatag cagtacctga                               30

<210> SEQ ID NO 13
<211> LENGTH: 108
<212> TYPE: DNA
<213> ORGANISM: Artificial Sequence
<220> FEATURE:
<223> OTHER INFORMATION: Description of Artificial Sequence: Solid
      Phase Synthesis of Nucleic Acid Probe Complementary to
      mecA Gene from Staphylococcal Species

<400> SEQUENCE: 13
gacgataata gcaatacaat cgcacataca ttaatagaga aaagaaaaa agatggcaaa    60 gatattcaac taactattga tgctaaagtt caaaagagta tttataac              108

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Solid
      Phase Synthesis of Nucleic Acid Probe Complementary to
      mecA Gene from Staphylococcal Species

<400> SEQUENCE: 14
atacattaat agagaaaaag aaaaaagatg gcaaag                        36

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Solid
      Phase Synthesis of Nucleic Acid Probe Complementary to
      mecA Gene from Staphylococcal Species

<400> SEQUENCE: 15
atacattaat agagaaaaag aaaaaagatg gcaaag                        36

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Solid -continued Phase Synthesis of Nucleic Acid Probe Complementary to
    mecA Gene from Staphylococcal Species

<400> SEQUENCE: 16
acggagaaga agttgtagca gg                                              22

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 17
ggtgaagtag aaatgactga acgtccg                                         27

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 18
aagatggtat gtggaagtta gattg                                           25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 19
gatggtatgt ggaagttaga ttgg                                            24

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 20
tggtatgtgg aagttagatt gggatc                                          26

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence:  Solid
      Phase Synthesis of Nucleic Acid Probe Complementary to
      mecA Gene from Staphylococcal Species

<400> SEQUENCE: 21
atgcagttat tggtaaaaag ggactcg                                         27

<210> SEQ ID NO 22

```
<211> LENGTH: 23
<212> TYPE: DNA
<213> ORGANISM: Artificial Sequence
<220> FEATURE:
<223> OTHER INFORMATION: Description of Artificial Sequence: Solid
      Phase Synthesis of Nucleic Acid Probe Complementary to
      mecA Gene from Staphylococcal Species

<400> SEQUENCE: 22
tgtttgaggg tggatagcag tac                                           23

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Solid
      Phase Synthesis of Nucleic Acid Probe Complementary to
      mecA Gene from Staphylococcal Species

<400> SEQUENCE: 23
gauaacauuu ucuuugcuag aguag                                         25

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Solid
      Phase Synthesis of Nucleic Acid Probe Complementary to
      mecA Gene from Staphylococcal Species

<400> SEQUENCE: 24
caagtcgtaa ataaaacaca taaagaag                                      28

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Solid
      Phase Synthesis of Nucleic Acid Probe Complementary to
      mecA Gene from Staphylococcal Species

<400> SEQUENCE: 25
tacaagataa aggaatggct agcta                                         25

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Solid
      Phase Synthesis of Nucleic Acid Probe Complementary to
      mecA Gene from Staphylococcal Species

<400> SEQUENCE: 26
gctagctaca atgccaaaat ctcaggt                                       27
```

METHODS FOR RAPIDLY DETECTING METHICILLIN RESISTANT STAPHYLOCOCCI

REFERENCE TO RELATED APPLICATIONS

This application claims the benefit of U.S. Provisional Patent Application No. 60/051,643, filed Jul. 3, 1997; 60/086,020, filed May 18, 1998; and 60/090,276, filed Jun. 22, 1998, each of which is incorporated herein by reference.

TECHNICAL FIELD

The present invention relates generally to medical diagnostics, and more specifically, to methods, probes and primers for detecting the mecA gene of methicillin resistant staphylococci.

BACKGROUND OF THE INVENTION

Methicillin-resistant *Staphylococcus aureus* (MRSA) is an extremely virulent antibiotic-resistant form of *Staphylococcus aureus* which has been rapidly spreading worldwide. MRSA has been found to be common in many hospitals, with a prevalence ranging from less than 1% to greater than 80% (Pittet and Waldvogel, *Q. J. Med.* 239–241, 1997). Unfortunately, MRSA is no longer considered only a hospital associated pathogen, since community-acquired MRSA is also increasing.

Resistance to methicillin by *Staphylococcus aureus* is caused by the expression of a low affinity penicillin binding protein (PBP) called PBP2a or PBP2', in addition to the usual PBPs (Hartman and Tomasz, *J. Bacteriol.* 158:513–516; 1984; Murakami and Tomasz, *J. Bacteriol.* 171:874–879, 1989). The responsible mecA gene which encodes the PBP2', mecA, is present in resistant strains but not susceptible ones (Hartman and Tomasz, *J. Bacteriol.* 158:513–516, 1984; Matsuhashi et al., *J. Bacteriol.* 167: 975–980, 1986), and has only a slight sequence variation from strain to strain (Ryffel et al., *Gene* 94:137–138, 1990). MRSA strains carrying the mecA gene also tend to demonstrate resistance to other antibiotics such as aminoglycosides, macrolides, quinolones, beta-lactams, monobactams, imipenem, meropenem (Maple et al., *Lancet* I:537–540, 1989; Kayser, *Chemotherapy* 42 (*suppl* 2):2–12; Chambers et al. cited in Bowler, *Q. J Med.* 90:243–246, 1997).

Some *S. aureus* strains may exhibit heterogeneity of expression of the mecA gene (Hartman et al., *Antimicrob. Agents Chemother.* 29:85–92, 1986; Hiramatsu et al., *Microbiol. Immunol.* 36:445–453, 1992; Ryffel et al., Antimicrob. Agents Chemother. 38:724–728, 1994). Within these populations, although all cells carry mecA, the majority of cells are susceptible to low concentrations of the antibiotic and only a minority of the cells (1 in 105–106 ) express resistance (Hackbarth et al., *Antimicrob. Agents Chemother.* 33:991–994, 1989; Ryffel et al., *Antimicrob. Agents Chemother.* 38:724–728, 1994). Consequently, these strains exhibit low MIC and may be incorrectly characterized as sensitive to methicillin. Conversely, some *S. aureus* strains that lack the mecA gene may display borderline or low level resistance to methicillin due to alternate mechanisms of resistance (Chambers et al., *Antimicrob. Agents Chemother.* 33:424–428, 1989; Hiramatsu et al., Supra). Low level resistance to methicillin due to hyper β-lactamase production, methicillinase production, or the synthesis of modified PBP (Knapp, et al, *J. Clin. Microbiol.* 34:1603–1605, 1996; McDougal, et al., *J. Clin. Microbiol.* 23:832–839, 1986; Tomasz et al., *Antimicrob. Agents Chemother.* 33:1869–1874, 1989.) may be incorrectly diagnosed as MRSA by conventional susceptibility tests.

Rapid detection, both for prevention of transmission and treatment of methicillin resistant Staphylococcus (MRS) species has become a worldwide priority. There are a number of techniques available in the diagnostic field for detecting MRS, including conventional biochemical tests and immunological tests. For example, one accepted method for detection of MRS is the screening for isolates on Mueller-Hinton agar containing 4% NaCl and 6 µg/ml of oxacillin. Many laboratories now use automated screening systems such as Microscan API (Dade) and Vitek GPS-SA card (bioMerieux, Hazlewood, Mo.) which give susceptibility results within 24 hours (Knapp et al., Supra). The BBL® Crystal™ MRSA ID test (Beckton Dickinson, Cockeysville, Md.) is a more rapid susceptibility test that permits diagnosis after 4 to 6 hours (Wallet et al. *J. Antimicrobiol. Chemother.* 37:901–909; Martinez et al, *Rev. Esp. Quimioterap.* 9:130–133, 1996). However, none of the susceptibility tests can reliably differentiate between heterogeneous MRSA and borderline oxacillin resistant *S. aureus* (BORSA, Knapp et al., Supra; Lencastre et al., *Eur. J. Clin. Microbiol. Infect. Dis.* 12:S13–S18).

Many of these techniques also have drawbacks related to time, lack of specificity and sensitivity of detection. To address such issues, detection of the mecA gene utilizing the polymerase chain reaction ("PCR") has also been attempted. Briefly, PCR has been used in several studies for detecting the mecA gene, but test results using this method are expensive and can take up to 6 hours (Wallet, Supra). In addition, there are a number of problems associated with such methods, including background contamination, carry over contamination, thermocycling, special room requirements, cumbersome from the point of view of the number of primers and probes required, number of steps and time involved in processing the samples and the special training required. In spite of the wide use of PCR in the molecular biology area due to its high sensitivity and multiple applications there are only a few FDA approved PCR or other target amplification based diagnostic products. The main factor limiting the use of these technologies in clinical diagnostic setting is the inherent problem of amplicon contamination. There are several chemical or physical methods that were developed to reduce or eliminate the problem of contamination. Generally these methods add extra steps and are costly.

Although the above methods can be used to detect MRSA, there is an urgent need for a rapid, user friendly and reliable method for detecting the mecA gene in nosocomial and non-nosocomial settings. The present invention provides probes, primers and methods for detecting the mecA gene that meet these needs. Further, the present invention provides other, related advantages.

SUMMARY OF THE INVENTION

Briefly stated, the present invention provides compositions and methods for detecting the mecA gene of the methicillin resistant staphylococci.

Within one aspect of the present invention, methods are provided for determining the presence of an antibiotic resistant mecA gene in a biological sample, comprising the steps of (a) treating cells contained within a biological sample to expose target single-stranded nucleic acid molecule, (b) reacting target single-stranded nucleic acids with a scissile link-containing nucleic acid probe which is complementary to a portion of an antibiotic resistant mecA gene, and with an enzyme which cleaves double-stranded target-probe complexes, under conditions which allow the target and probe to hybridize to each other to form a double-stranded target-probe complex, the enzyme molecule being capable of cleaving the scissile link of the target-probe complex such that one or more fragments of the nucleic acid probe released from said complex, and (c) determining whether cleaved portions of the nucleic acid probe are produced, and thereby detecting the presence of an antibiotic resistant mecA gene. Within various embodiments, determination of whether cleaved probe is produced can be accomplished by directly detecting cleaved portions of the nucleic acid probe, and/or detecting a decrease in the amount of uncleaved probe.

Within one embodiment, the probe comprises at least a portion of the nucleotide sequence GACGATAATA GCAATACAAT CGCACATACA TTAATAGAGA AAAAGAAAAA AGATGGCAAA GATATTCAAC TAACTATTGA TGCTAAAGTT CAAAAGAGTA TTTATAAC (SEQ ID NO:13). Within a further embodiment, the probe consists essentially of at least a portion of the nucleotide sequence GAACTTTAGC ATCAATAGTT AGTTGAATAT CTTTGCCATC TTTTTTCTTT TTCTCTATTA ATGTATGTGC GATTGTATTG CTATTATCG (SEQ ID NO:4). Other representative probes include: AATAGAGAAA AAGAAAAAAG ATGGCAAAG (SEQ ID NO:1); and AATAGAGaaaaAGAAAAA AGATGGCAAAG-3'(SEQ ID NO:5) wherein large letters represent deoxyribonucleotides and small letters represent ribonucleotides. As utilized herein, a probe should be at least 8 nucleotides in length, and may be 10, 12, 14, 15, 16, 18, 20, 30 or even 100 or more nucleotides in length.

Within various embodiments, the mecA gene is from a staphylococcal species, either coagulase positive (e.g., *S. aureus*), or coagulase negative (e.g., *S. epidermidis, S. sciuri*).

Within other related aspects of the present invention, probes for detecting the present of an antibiotic resistant mecA gene in a biological sample are provided, wherein said probe comprises at least a portion of the sequence GACGATAATA GCAATACAAT CGCACATACA TTAATAGAGA AAAAGAAAAA AGATGGCAAA GATATTCAAC TAACTATTGA TGCTAAAGTT CAAAAGAGTA TTTATAAC (SEQ ID NO:13). Also provided are kits which comprise such probes, along with an enzyme (e.g., RNase H) which cleaves scissile links.

Within further aspects, kits are provided for detecting the presence of an antibiotic resistant mecA gene in a biological sample, comprising (a) one or more scissile-link containing nucleic acid probes, and (b) an enzyme capable of cleaving the scissile link when the probe is bound to a target. Within various embodiments, the enzyme is RNase H. Within further embodiments, the mecA gene is from a staphylococcal species.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

DETAILED DESCRIPTION OF THE INVENTION

Definitions

Figure 1:
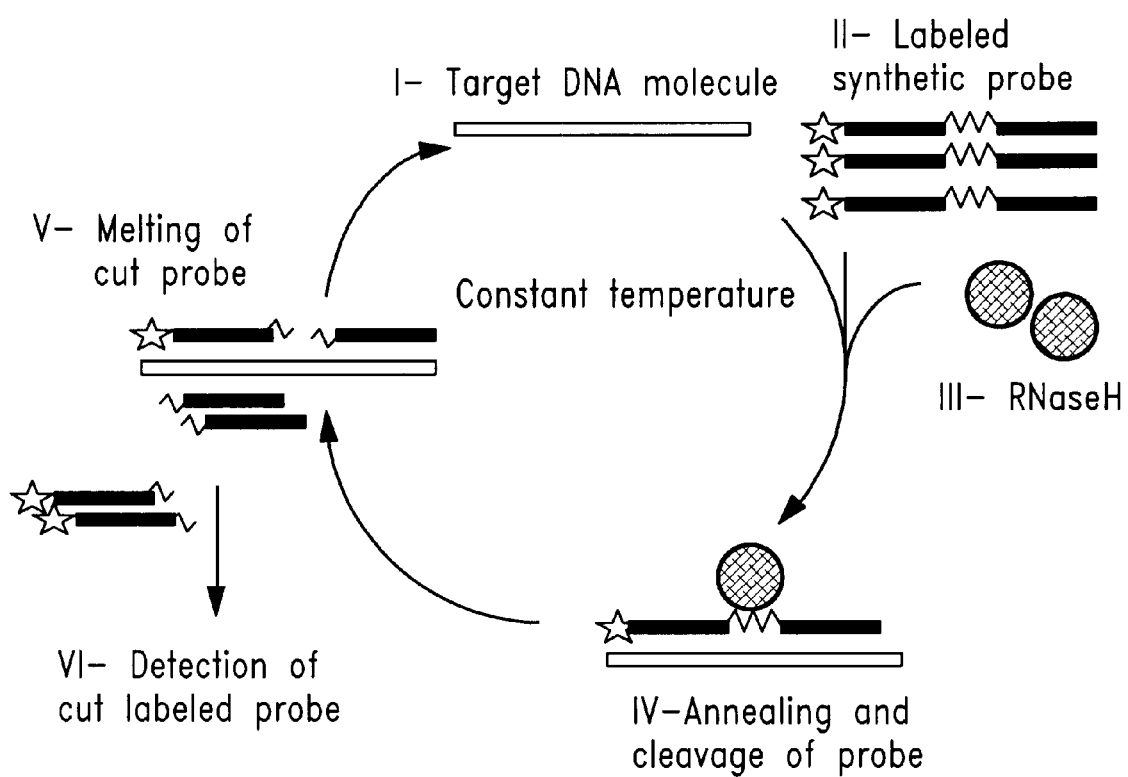
FIG. 1 is a schematic illustration of one embodiment of a cycling probe reaction.

"Nucleic acid molecule" refers to a polymeric nucleotide or polynucleotide, which can be of either a natural or synthetic origin. Representative examples of nucleic acid molecules include DNA (ds- or ss-DNA), RNA, DNA-RNA hybrids, or nucleic acid molecules which are composed of or contain a nucleic acid analogues (e.g., a-enantiomeric forms of naturally-occurring nucleotides). Furthermore, nucleotides may be modified in their sugar moieties, or in the pyrimidine or purine base moieties. Examples of modification to sugar moieties include modification or replacement of, for example, one or more hydroxyl groups with another group. Modifications to base moieties include alkyl or acylated pyrimidines and purines. In addition, nucleic acid monomers can be linked by phosphodiester bonds, or analogs of such linkages (e.g., phosphorothioate, phosphorodithioate, phosphoramidite, and the like.).

"Isolated nucleic acid molecule" refers to a nucleic acid molecule that is not integrated into the genomic DNA of an organism. Isolated nucleic acid molecules include, for example, probes and other synthetically or recombinantly generated nucleic acid molecules.

"Scissile linkage" refers to a nucleic acid molecule which is capable of being cleaved or disrupted without cleaving or disrupting any nucleic acid sequence of the molecule itself or of the target nucleic acid sequence. Scissile linkages include any connecting chemical structure which joins two nucleic acid sequences and which is capable of being selectively cleaved without cleavage of the nucleic acid sequences to which it is joined. The scissile linkage may be a single bond or a multiple unit sequence. An example of such a chemical structure is an RNA sequence. Other chemical structures suitable as a scissile linkage are a DNA sequence, an amino acid sequence, an abasic nucleotide sequence or an abasic nucleotide, or any carbohydrate polymer, i.e., cellulose or starch. When the scissile linkage is a nucleic acid sequence, it differs from the nucleic acid sequences of $NA_1$ and $NA_2$ (described below).

"Probe Containing a Scissile Linkage" refers to a synthetic nucleic acid molecule which is constructed in view of a known sequence to be complementary or substantially complementary to a target nucleic molecule. Within certain embodiments, the probe comprises the structure $[NA_1\text{--S--}NA_2]_n$ wherein $NA_1$ and $NA_2$ are different, non-complementary nucleic acid molecules and S is a scissile linkage, and n is an integer from 1 to 10.

"Ribonuclease H" ("RNase H") refers to an enzyme capable of specifically cleaving the RNA strand in RNA:DNA hybrid duplex (see generally Crouch & Dirkensen in Nucleases, Linn & Roberts (Eds.), pp. 211–241, Cold Spring Harbour Laboratory Press, Plainview, N.Y., 1982).

Thus, as noted above, methods are provided for determining the presence of an antibiotic resistant mecA gene in a biological sample, comprising the steps of (a) treating cells contained within a biological sample to expose target single-stranded nucleic acid molecules, (b) reacting the target single-stranded nucleic acids with a scissile link-containing nucleic acid probe which is complementary to a portion of an antibiotic resistant mecA gene, and with an enzyme which cleaves double-stranded target-probe complexes, under conditions which allow the target and probe to hybridize to each other to form a double-stranded target-probe complex, the enzyme molecule being capable of cleaving said scissile link of said target-probe complex such that one or more fragments of the nucleic acid probe are released from said complex, and (c) determining whether cleaved portions of the nucleic acid probe are produced, and thereby detecting the presence of an antibiotic resistant mecA gene. Utilizing such methods, one of skill in the art can generate accurate and rapid results which can provide same day results from test samples. This allows appropriate utilization of antibiotics for the patients, thereby reducing use of vancomycin. Further more, such methods may be readily utilized to monitor outbreaks or for routine surveillance in both nosocomial and non-nosocomial settings.

Such methods may be utilized to detect the presence of a desired target nucleic acid molecule within a biological sample. Representative examples of biological samples include cultured (e.g., growing a bacteriological medium) or clinical samples, including for example, samples from nasal swabs, blood, urine, stool, abscess or spinal fluids. Methods for generating target nucleic acid molecules may be readily accomplished by one of ordinary skill in the art given the disclosure provided herein (see generally, Sambrook et al., *Molecular Cloning: A Laboratory Manual* (2d ed.), Cold Spring Harbor Laboratory Press, 1989).

As noted above, within one aspect of the present invention the target nucleic acid molecule is reacted with a complementary single-stranded nucleic acid probe having a scissile linkage. Briefly, a wide variety of nucleic acid probes having scissile linkages may be utilized within the context of the present invention. Preferably, the probe is designed such that, upon cleavage by an enzyme which is capable of specifically cleaving the probe-target complex at the scissile link, probe portions are released which are detectable (see U.S. Pat. Nos. 4,876,187, 5,011,769 and 5,403,711).

Preferred probe molecules of the present invention generally have the structure $[(NA_1)_x(\text{-S-})_z(\text{-}NA_2)y]_n$ wherein $NA_1$ and $NA_2$ are molecules composed of nucleic acids or nucleic acid analogues, -S- is a scissile linkage and x, y, and z are integers from 1–100 and n is an integer from 1–10. Within certain particularly preferred embodiments of the invention, $NA_1$ and $NA_2$ may range from 3 to 40 nucleotides, and when S is composed of nucleic acids, may range in size from 2 to 20 nucleotides. In addition, it should be understood that as utilized within the context of the present invention, each of x, y and z can vary with each iteration of n. Although within various embodiments of the invention a single-stranded probe is utilized to react or hybridize to a single-stranded target sequence, the above-described methods should not be limited to only situations wherein complementary probe and target sequences pair to form a duplex.

Single stranded nucleic acid molecules may be obtained and/or prepared directly from a target cell or organism utilizing standard techniques (see, e.g., Sambrook et al., "Molecular Cloning: A Laboratory Manual", Cold Spring Harbor, 1989), or prepared utilizing any of a wide variety of a techniques, including for example, PCR, NASBA, reverse transcription of RNA, SDA, branched-chain DNA and the like.

Within one embodiment, $NA_1$ and $NA_2$ as described above are DNA molecules which may or may not have the same sequence. Alternatively, $NA_1$ and $NA_2$ may be constructed of RNA molecules, which may or may not have the same sequence, or a combination of RNA and DNA molecules. The DNA or RNA molecules utilized may be derived from naturally occurring sources, or they may be synthetically formed. Each of $NA_1$ and $NA_2$ may be from about 5 bases to 10,000 bases in length. Within certain variants, the probe and target nucleic acid molecule need not be perfectly complementary, and indeed, may be purposely different by one, two, three or more nulcleic acids (see, e.g., PCT Publication WO 95/14106 and U.S. Pat. No. 5,660,988). Within further variants, the target nucleic acid molecule is present in a heterogeneous population of genomic nucleic acids.

Within other embodiments, $NA_1$ or $NA_2$ may be composed of nucleic acid analogues such as methyl phosphonates, carbamates, amidates, triesters, or "Peptide Nucleic Acids" ("PNA"). For example, PNA oligomers can hybridize to complementary target oligonucleotides (DNA or RNA) sequences with very high specificity. Such duplexes are more stable than the corresponding DNA-DNA or DNA-RNA duplexes (Egholm et al., *Nature* 365:556–568, 1993). Furthermore, PNA can bind to double stranded (ds) DNA by strand displacement (Nielsen et al., *Science* 254:1497–1500, 1991) and hence may obviate the traditional double strand denaturation requirement in sample preparation. Low concentration salt is generally preferred for binding of PNA to dsDNA ($\leq 50$ mM/L of $Na^+$). Moderate concentration of salt can inhibit binding through double strand displacement of PNA to dsDNA. However, once bound the PNA/DNA duplexes are stable to high concentration of salt. Further, these duplexes are also thermally stable compared to oligonucleotide/oligonucleotide duplexes (duplexes of PNA/DNA are more stable by approximately 1° C. per base pair compared to corresponding DNA/DNA). Based on the requirement of high sequence specificity to the target oligonucleotide, greater thermal stability and resistance to high salt concentration of the duplex once formed, PNAs are often ideal molecules for use in the methods described herein. Within certain embodiments, two short PNAs may be linked with scissile linkage and used as a highly sequence specific probe.

Probes of the present invention may also have one or more detectable markers attached to one or both ends (e.g., $NA_1$ or $NA_2$). The marker may be virtually any molecule or reagent which is capable of being detected, representative examples of which include radioisotopes or radiolabeled molecules, fluorescent molecules, fluorescent antibodies, enzymes, or chemiluminescent catalysts. Within certain embodiments of the invention, the probe may contain one or more labels such as a fluorescent or enzymatic label (e.g., quenched fluorescent pairs, or, a fluorescent label and an enzyme label), or a label and a binding molecule such as biotin (e.g., the probe, either in its cleaved or uncleaved state, may be covalently or non-covalently bound to both a label and a binding molecule (see also, e.g., U.S. Pat. No. 5,731,146).

As noted above, the nucleic acid probe has a scissile linkage which is capable of being cleaved or disrupted without cleaving or disrupting any nucleic acid sequence of the molecule itself, or of the target nucleic acid sequence. As used within the context of the present invention, a scissile linkage is any connecting chemical structure which joins two nucleic acid sequences, and which is capable of being selectively cleaved without cleavage of the nucleic acid sequences to which it is joined. The scissile linkage may be a single bond or a multiple unit sequence. An example of such a chemical structure is an RNA molecule. Other chemical structures which may be suitable as a scissile linkage are DNA molecules, an amino acid sequence, an abasic nucleotide molecule or any carbohydrate polymer (e.g., cellulose or starch). When the scissile linkage is a nucleic acid molecule, it should differ from the nucleic acid sequence of $NA_1$ and $NA_2$.

In the nucleic acid probes described above, when n is greater than one, the unit $NA_1$-S-$NA_2$ repeats. As should be readily understood by one of ordinary skill in the art given the disclosure provided herein, the unit may be the same within each repeat, or may vary randomly in a defined pattern. In addition, the scissile linkage may also vary from unit to unit. For example, one scissile linkage may be an amino acid sequence, and another an RNA molecule.

As noted above, the probes of the present invention may also be linked to a solid support either directly, or through a chemical linker. Representative examples of solid supports include silicaceous, cellulosic, polymer-based, or plastic materials.

Within a particularly preferred embodiment of the invention, nucleic acid probes have the structure: $[NA_1\text{-S-}NA_2]_n$ wherein $NA_1$ and $NA_2$ are nucleic acid sequences, S is a scissile nucleic acid linkage, and n is an integer from 1 to 10. Within this embodiment, $NA_1$ and $NA_2$ are different nucleic acid sequences which are noncomplementary to each other, and -S- is a scissile linkage which is capable of being cleaved or disrupted without cleaving or disrupting $NA_1$ or $NA_2$, or a target nucleic acid sequence capable of hybridizing to the $NA_1$ or $NA_2$ sequences, wherein if the scissile linkage is a nucleic acid sequence it is RNA when both $NA_1$ and $NA_2$ are DNA sequences, or the scissile linkage is DNA when both $NA_1$ and $NA_2$ are RNA sequences.

Methods for constructing such nucleic acid probes may be readily accomplished by one of ordinary skill in the art, given the disclosure provided herein. Particularly preferred methods are described for example by: Matteucci and Caruthers, *J. Am. Chem. Soc.* 103:3185,1981; Beaucage and Caruthers, *Tetrahedron Lett.* 22:1859–1862, 1981; U.S. Pat. Nos. 4,876,187 and 5,011,769; Ogilvie et al., *Proc. Natl. Acad. Sci. USA* 85:8783–8798, 1987; Usman et al., *J. Am. Chem. Soc.* 109:7845–7854, 1987; Wu et al., *Tetrahedron Lett.* 29:4249–4252, 1988; Chaix et al., *Nuc. Acids Res.* 17:7381–7393, 1989; Wu et al., *Nuc. Acids Res.* 17:3501–3517, 1989; McBride and Caruthers, *Tetiahedron Lett.* 24:245–248, 1983; Sinha et al., *Tetrahedron Lett.* 24:5843–5846, 1983; Sinha et al., *Nuc. Acids Res.* 12:4539–4557, 1984; and Gasparutto et al., *Nuc. Acids Res.* 20:5159–5166, 1992.

Particularly preferred probes (and synthetic targets) are based on the *S. aureus* mecA gene described by Song et al., *FEBS Letters* 221: 167–171, 1987 (EMBL Accession No. Y00688). DNA sequences of mecA from different MRSA strains show only minor variations (Ryffel et al., *Gene* 94:137–138, 1990, *S. aureus* EMBL Accession No. X52593 and *S. epidermidis* EMBL Accession No. X52592). The mecA gene is also distributed among the coagulase-negative Staphylococci and associated with methicillin resistance (cited in Kobayashi et al,. *Epidemiol. Infect.* 113:259–266, 1994).

Single probes can be designed to detect the mecA gene generally by choosing conserved regions or use of universal bases or abasic sites or other modifications as described in U.S. Provisional Application No. 60/086,022.

Briefly, oligonucleotide synthesis is accomplished in cycles wherein each cycle extends the oligonucleotide by one nucleotide. Each cycle consists of four steps: (1) deprotecting the 5'-terminus of the nucleoside or oligonucleotide on the solid support, (2) coupling the next nucleoside phosphoramidite to the solid phase immobilized nucleotide, (3) capping the small percentage of the 5'-OH groups of the immobilized nucleotides which did not couple to the added phosphoramidite, and (4) oxidizing the oligonucleotide linkage to a phosphotriester linkage.

Representative methods for synthesizing oligonucleotides and biotinylation and fluoresceination of the oligonucleotides are shown in Example 1.

Detection Reactions

As noted above, wide variety of cycling reactions for the detection of a desired target nucleic acid molecule may be readily performed according to the general steps set forth above (see also, U.S. Pat. Nos. 5,011,769 and 5,403,711).

Within one aspect, such methods generally comprise the steps of (a) treating cells contained within a biological sample to expose target single-stranded nucleic acid molecule, (b) reacting target single-stranded nucleic acids with a scissile link-containing nucleic acid probe which is complementary to a portion of an antibiotic resistant mecA gene, and with an enzyme which cleaves double-stranded target-probe complexes, under conditions which allow the target and probe to hybridize to each other to form a double-stranded target-probe complex, the enzyme molecule being capable of cleaving the scissile link of the target-probe complex such that one or more fragments of the nucleic acid probe released from said complex, and (c) determining whether cleaved portions of the nucleic acid probe are produced, and thereby detecting the presence of an antibiotic mecA gene. Within other related aspects, the compositions and methods provided herein may be utilized in a wide variety of other/related methods (e.g., U.S. Pat. Nos. 5,210,015; 5,487,972; 5,422,253; 5,691,142; 5,719,028; 5,130,238; 5,409,818; 5,554,517; 5,589,332; 5,399,491; 5,480,784; 5,215,899; 5,169,766; 5,194,370; 5,474,916; 5,698,400; 5,656,430; and PCT publication nos. WO 88/10215; WO 92/08800,, WO 96/02668; WO 97/19193; WO 97/09444; WO 96/21144; WO 92/22671).

Within certain embodiments of the invention, the detection reactions provided herein may be performed utilizing additives such as polyamines (e.g., spermine) or ribosomal proteins which increase sensitivity, specificity, and/or rate of reaction. These, as well as other related aspects are described in U.S. Provisional Application Nos. 60/086,026 and 60/086,021.

In another embodiment CPT can be used for detecting amplicons generated by any target amplification technology. Example 10 illustrates the use of CPT enzyme immunoassay (CPT-EIA) for the detection of PCR amplicons. CPT allows rapid and accurate detection of PCR amplicons. In addition, CPT adds a second level of amplification but without further amplifying the target, and therefore it is possible to use significantly less number PCR cycles. This will reduce the chance of contamination and false positive. CPT adds a second level of specificity which will prevent detection of non-specific amplicons and primer-dimers. The PCR-CPT method may also be used for mismatch gene detection. Other variations of this assay include 'exponential' cycling reactions such as described in U.S. Pat. No. 5,403,711 (see also U.S. Pat. No. 5,747,255).

Lateral flow device (strip or dipstick) as described in U.S. Pat. Nos. 4855240 and 4703017, for example, represents another embodiment for detection format for the MRSA assay. Instead of detecting uncleaved mecA probe on streptavidin coated wells (i.e., EIA format), the uncleaved probe is captured by streptavidin impregnated on a membrane (i.e., strip format). There are several advantage for using this format. There are no additional detection reagents required, less hands-on time, and a short detection time. Representative examples of further suitable assay formats including any of the above assays which are carried out on solid supports such as dipsticks, magnetic beads, and the like (see generally U.S. Pat. Nos. 5,639,428; 5,635,362; 5,578,270; 5,547,861; 5,514,785; 5,457,027; 5,399,500; 5,369,036; 5,260,025; 5,208,143; 5,204,061; 5,188,937; 5,166,054; 5,139,934; 5,135,847; 5,093,231; 5,073,340; 4,962,024; 4,920,046; 4,904,583; 4,874,710; 4,865,997; 4,861,728; 4,855,240; and 4,847,194).

In another embodiment, CPT can be carried out using the exponential formats with two sets of nucleic acid probe molecules which are immobilized on solid support as described in U.S. Pat. No. 5,403,711. This would be advantageous since the assay can be carried out in a single container, the signal can be monitored over time and would result in a very rapid and sensitive assay.

In yet another embodiment CPT-EIA can be used for detecting for MRSA by use of reverse transcriptase to transcribe cDNA from MRNA expressed by the mecA gene followed by Cycling Probe Technology (RT-CPT) as described in U.S. Pat. No. 5,403,711. The uncleaved probe specific the cDNA can than be detected by EIA.

The following examples are offered by way of illustration, and not by way of limitation.

EXAMPLES

Example 1

Construction of Nucleic Acid Probes

Nucleic acid molecules can be synthesized utilizing standard chemistries on automated, solid-phase synthesizers such as PerSeptive Biosystems Expedite DNA synthesizer (Boston, Mass.), PE Applied Biosystems, Inc.'s Model 391 DNA Synthesizer (PCR-MATE EP) or PE Applied Biosystems, Inc.'s Model 394 DNA/RNA Synthesizer (Foster City, Calif.). Preferably, PerSeptive Biosystems Expedite DNA synthesizer is used and the manufacturer's modified protocol for making oligonucleotides is carried out.

Reagents for synthesis of oligonucleotides are commercially available from a variety of sources including synthesizer manufacturers such as PerSeptive Biosystems, PE Applied Biosystems Inc., Glen Research (Sterling, Va.) and Biogenex. For DNA and RNA synthesis, the preferred fluorescein amidite, phosphoramidites of deoxy- and ribonucleosides, 2'-O-methyl and reagents, such as activator, Cap A, Cap B, oxidizer, and trityl deblocking reagent are available from PerSeptive Biosystems. Biotin-TEG-phosphoroamidite and Biotin-TEG-CPG are available from Glen Research. Ammonium hydroxide (28%) used for the deprotection of oligonucleotides is purchased from Aldrich. 1 M Tetrabutylammonium fluoride (TBAF) used for removing the 2'-O-tert-butyldimethylsilyl group is purchased from Aldrich and used after drying over molecular sieves for 24 hours. All buffers are prepared from autoclaved water and filtered through 0.2 $\mu$m filter.

The following procedure is used for preparing biotinylated and/or fluoresceinated oligonucleotides. Biotin-TEG-CPG (1 $\mu$mol) is packed into a synthesis column. Nucleoside phosphoramidites are then linked to make the defined nucleic acid sequence using PerSeptive Biosystem's modified protocol for making oligonucleotides. Fluorescein-amidite is dissolved in acetonitrile to a final concentration of 0.1 M. The fluorescein amidite is loaded on the synthesizer and added to the 5'-end of the oligonucleotide. Alternatively, phosphoramidite containing thio-linker is added at the 5'-terminal of the chimeric probe using the modified protocol. After the deprotection step described below, the probe is purified by reverse phase HPLC using Millipore's R-2 resin which retains the trityl containing oligonucleotide. In order to generate free reactive thio-group, the HPLC purified probe is treated with silver nitrate for 90 minutes at room temperature followed by neutralization of silver nitrate with dithiotheritol (DTT). The fluorescein-supernatant is then added to the free thio-group of the probe and then purified either by HPLC or by electrophoresis as described below.

After the synthesis of the oligonucleotide sequence, the resin bound oligonucleotide is treated initially with 25% ethanol-ammonium hydroxide (4 ml) at room temperature for 1 hour and subsequently at 55° C. for 16 hours in a closed tube. The tube is cooled, supernatant removed and concentrated to dryness in order to remove ammonia. The residue is dissolved in 1 ml of water and filtered through a 0.2 μm filter. The $OD_{260}$ is determined and an aliquot of approximately 2 $OD_{260}$. units is injected into the R-2 column of Biocad's HPLC to obtain a base line on the chromatogram for the tert-butyldimethylsilyl groups of the chimeric probe.

The remaining probe solution is lyophilized by centrifugal vacuum evaporator (Labconco) in a 1.5 ml microcentrifuge tube. The resulting oligonucleotide residue is deprotected with 1.0 M TBAF for 24 hours. To determine the extent of desilylation which has taken place, an aliquot of the TBAF reaction mixture is injected into the HPLC (R-2 column) using a linear gradient of 0 to 60% acetonitrile in 50 mM triethylammonium acetate (TEAA), pH 6.5. If only a partial desilylation has occurred, the TBAF reaction mixture is allowed to proceed for an additional 12 to 16 hours for complete removal of the protecting groups. The TBAF reaction mixture is quenched with 100 mM NaOAc, pH 5.5 and evaporated to dryness. The crude oligonucleotide product is desalted on a P-6 column (2 cm×10 cm, Bio-Rad), the fractions are concentrated to approximately 1 ml and the concentration measured at $OD_{260}$.

The crude oligonucleotide is purified by polyacrylamide gel electrophoresis (PAGE) using 20% polyacrylamide-7 M urea. The running gel buffer is 1×TBE (Tris-Borate-ethylenediamine tetraacetic acid (EDTA), pH 8.3 ) and the electrophoresis is carried out at 50 mA current for 3.5 to 4 hours. The oligonucleotide band is visualized with UV light, excised, placed in a 15 ml plastic conical tube and extracted by crushing and soaking the gel in 5 ml of 50 mM NaOAc (pH 5.5) for approximately 12 hours. The tubes are then centrifuged at 3000 RPM and the supernatant carefully removed with a Pasteur pipette. The gel is rinsed with 2 ml of the extraction buffer to remove any residual product. The combined extract is concentrated to a volume of approximately 1 ml and desalted on a P-6 column. The fractions containing the probe are pooled and concentrated to a final volume of approximately 2 ml. The analytical purity of oligonucleotides is checked by labeling the 5'-end of oligonucleotide with [$\gamma^{32}$P]-ATP and T4-polynucleotide kinase and then running the labeled oligonucleotide on PAGE. $OD_{260}$ is measured using Hewlett Packard's 845X UV spectrophotometer. The oligonucleotide solution is filtered through a 0.2 μm filter and stored at −20° C.

Utilizing the above procedure, the following oligomers can be synthesized. In these sequences, upper case letters have been utilized to denote deoxyribonucleotides, lower case letters to denote ribonucleotides, underlined letters to denote 2'-O-methyl linkages, upper case letter F to denote fluorescein label, upper case letter B to denote Biotin, upper case letters XL to denote the XL linker (available from Glen Research or Clontech), and subcase numeral to denote repeats of indicated moiety.

mecA945–29D (SEQ ID NO:1)
5'-AAT AGA GAA AAA GAA AAA AGA TGG CAA AG-3' mecA945T (SEQ ID NO:2)
5'-CTT TGC CAT CTT TTT TCT TTT TCT CTA TT-3' mecA932–59R (SEQ ID NO:3)
5'-cgc aca uac auu aau aga gaa aaa gaa aaa aga ugg caa aga uau uca acu aac uau ug-3' ccmecA915–89 (SEQ ID NO:4)
5'-GAA CTT TAG CAT CAA TAG TTA GTT GAA TAT CTT TGC CAT CTT TTT
TCT TTT TCT CTA TTA ATG TAT GTG CGA TTG TAT TGC TAT TAT CG-3' mecA945–29 (SEQ ID NO:5)
5'-AAT AGA GAA AAA Gaa aaA AGA TGG CAA AG-3' mecA945–29A$_{18}$P (SEQ ID NO:6)
5'-AAT AGA GAA AAA Gaa aaA AGA TGG CAA AGA$_{18}$-3' mecA945–29(2'OMe) (SEQ ID NO:7)
5'-AAT AGA GAA AAA Gaa aaA AGA TGG CAA AG-3' mecA945–29R (SEQ ID NO:8)
5'-aau aga gaa aaa gaa aaa aga ugg caa ag-3' mecA834–25 (SEQ ID NO:9)
5'-TGG TAA AAA GGG ACT CGA AAA ACT T-3' mecAL1039–22 (SEQ ID NO:10)
5'-GGT GGA TAG CAG TAC CTG AGC C-3' mecA869–29 (SEQ ID NO: 11)
5'-AGC TCC AAC ATG AAG ATG GCT ATC GTG TC-3' mecAL1042–30 (SEQ ID NO:12)
5'-ACC TGT TTG AGG GTG GAT AGC AGT ACC TGA-3' mecA945–29B (SEQ ID NO:5)
5'-FAAT AGA GAA AAA Gaa aaA AGA TGG CAA AGB-3'

F-mecA945–29(XL)4B3 (SEQ ID NO:5)
5'-FAAT AGA GAA AAA Gaa aaA AGA TGG CAA AG(XL)$_4$B$_3$-3' mecA913–1020 (SEQ ID NO:13)
5'-GACGATAA TAGCAATACA ATCGCACATA CAT-TAATAGA GAAAAAGAAA AAAGATGGCA AAGATATTCA ACTAACTATT GATGCTAAAG TTCAAAAGAG TATTTATAAC-3' mecA938–36 (SEQ ID NO:14)
5'-ATACATTAATAGAGAAAAAGAAAAAAGATGGCA AAG-3' mecA938–36 (SEQ ID NO:15)
5'-ATACATTAATAGAGaaaaAGAAAAAAGATGGCAA AG-3'

Table of other mecA probes

| Probe name | Sequence ID No. | Sequence 5' to 3' |
|---|---|---|
| mecAL53–22 | SEQ ID NO:16 | ACGGAGAAgaagUGTAGCAGG |
| mecA172–27 | SEQ ID NO:17 | GGTGAAGTAgaaaTGACTGAACGTCCG |
| mecA356–25 | SEQ ID NO:18 | AAGATGGTATGTggaaGUAGAUG |
| mecA358–24 | SEQ ID NO:19 | GATGGTATGTggaaGUAGAUGG |
| mecA360–26 | SEQ ID NO:20 | TGGTATGTGgaagUAGAUGGGATC |
| mecA824–27 | SEQ ID NO:21 | ATGCAGTTAUGGTaaaaAGGGACTCG |
| mecAL1255–23 | SEQ ID NO:22 | TGTUGagggTGGATAGCAGTAC |
| mecA1393–25 | SEQ ID NO:23 | GAUAACAUUUucuuUGCUAGAGUAG 2'OMethyl, except for the ribonucleotides |
| mecA1735–28 | SEQ ID NO:24 | CAAGTCGTAAATaaaaCACATAAAGAAG |
| mecA1913–25 | SEQ ID NO:25 | TACAAGATAAAggaaTGGCTAGCTA |
| mecA1930–27 | SEQ ID NO:26 | GCTAGCTACAATGCCaaaaTCTCAGGT |

Example 2
Isotopic Cycling Probe Technology Reaction

Cycling probe technology (CPT) reaction and conditions are performed utilizing modified procedures from previously published methods (WO 95/14106; Bekkaoui et al., BioTechniques 20(2): 240–248, 1996). Briefly, a specified chimeric probe is 5'labeled with radioactive $^{32}$P using [$^{32}$P]-ATP (Du Pont, Sambrook et al., 1990) and T4 polynucleotide kinase (RTG; Pharmacia Biotech, Piscataway, N.J.). A single tube of RTG is resuspended in 15 μl of water. One pmol of probe is combined with 5 μl of γ-$^{32}$P ATP and 3 μl of RTG. The final volume is adjusted to 10 μl with water and incubated at 37° C. for 30 minutes. The unincorporated γ-$^{32}$P ATP is separated from the kinased probe by using a G50 Nick column (Pharmacia). The recovered probe is adjusted to 0.1× in SSC buffer (15 mM NaCl, 1.5 mM sodium citrate, pH 7.0) and stored at −20° C.

Unless otherwise indicated, the CPT reaction is carried out by adding in order, the following: TES cycling buffer, chimeric labeled probe, RNase H to give a cycling cocktail, which is then added to the denatured sample to be tested. The cycling reaction mixture contains the specified concentrations of chimeric probe, nucleic acid either as purified genomic DNA or crude lysate target, 3.3 μg RNase H in TES cycling buffer (TES-CB) which has the following final concentration: 0.05% Triton X-100®, 4 mM MgCl$_2$, 1 mM ethylenebis(oxyethylenitrilo)-tetracetic acid (EGTA), 20 mM TES buffer, pH 6.8. Sample preparations, addition of test additives, and other components used in the cycling reactions are described in the specific examples.

Unless otherwise specified, the CPT reactions are incubated for 30 minutes at 56° C. and then stopped by addition of urea loading buffer (8 M urea, 100 mM ethylenediamine tetracetic acid (EDTA) and 0.25% each of blue bromophenol and xylene cyanol, 80 mM phosphate buffer) at 56° C. The reaction mixtures are then resolved by 7 M urea-20% acrylamide/bisacrylamide (19:1) gel electrophoresis (SDS-PAGE) at 500 Volts, with cooling. The gel is analyzed on a PhosphorImager™ utilizing ImageQuant™ software (Molecular Dynamics, Sunnyvale, Calif.). The amount of cycled probe is estimated by integration of the areas of bands corresponding to intact and cleaved probe.

Unless otherwise stated, in a CPT reaction Percent Probe Cut is the total amount of cut probe relative to the total amount of the input probe (Equation No. 1):

$$\text{Percent Probe Cut} = (\text{Probe Cut/Total input probe}) \times 100 \qquad (1)$$

In a simple CPT system, the C1 background refers to the Percent Probe Cut in the reaction buffer without RNase H or homologous target present. C2 refers to Percent Probe Cut in the presence of RNase H but without homologous target (Equation No. 2):

$$C2 = (\text{Probe cut/Total input probe}) \times 100 \qquad (2)$$

For complex CPT system, C3 refers to Percent Probe Cut in the sample (biological samples that contains extraneous components, such as heterologous DNA or proteins) in the absence of RNase H. C4 refers to Percent Probe Cut in the biological sample in the presence of RNase H, but in the absence of homologous target (Equation No. 3):

$$C4 = (\text{Probe cut/Total input probe}) \times 100 \qquad (3)$$

Net Percent Probe Cut is the percent of probe cut due to homologous target and is calculated by subtracting the background C2 (simple system), or C4 (complex system) from the Percent Cut (Equations No. 4 or 5, respectively).

$$\text{Net Percent Probe Cut} = \text{Percent Cut} - C2 \qquad (4)$$

$$\text{Net Percent Probe Cut} = \text{Percent Cut} - C4 \qquad (5)$$

Signal to noise ratio (S:N) for CPT is defined as the ratio of the Percent Probe Cut in the presence of the homologous target to the C2 (simple system, Equation No. 6) or C4 (complex system, Equation No. 7):

$$S:N = \text{Percent Cut}/C2 \qquad (6)$$

$$S:N = \text{Percent Cut}/C4 \qquad (7)$$

Example 3
Preparation of Thermostable Rnase H

The following example describes one representative method for preparing thermostable RNase H from *Thermus thermophilus*.

The cloning of the thermostable gene and its expression is described in detail in WO 95/05480 and Bekkaoui et al., BioTechniques 20:240–248, 1996 based on the modification of the method by Kanaya & Itaya, *J. Biol. Chem.* 267:10184–10192, 1992. Briefly, the *T. thermophilus* RNase H gene (Kanaya & Itaya, Supra) is cloned by PCR into vector pT7-7 (pIDB9) and is subcloned into the vector PET11a (Novagen) resulting in the plasmid pIDB33. Plasmid pIDB33 is subsequently transformed into the bacterial strain BL21(DE3) (Novagen, Madison, Wis.). BL21(DE3) cells containing pIDB33 are grown at 37° C. in LB medium (Sambrook et al, 1990) containing 0.1 mg/ml ampicillin. When the culture is at an OD$_{600}$ of 0.6–0.8, IPTG is added to a final concentration of 0.5 mM and the cells are cultured for four more hours. RNase H is expressed in the inclusion bodies with the pIDB33 construct.

Cells are harvested by centrifugation at 3000× g for 15 minutes at 4° C. Cell pellets are resuspended at 1 g fresh weight in 5 ml of TE buffer (10 mM Tris, pH 7.4, 1 mM EDTA buffer). The cells are lysed in a dry ice/ethanol bath using a sonicator (Branson, model 450) and centrifuged at 15,000×g for 30 minutes at 4° C. The pellet is resuspended in 7 M urea in TE buffer, pH 8.0 and incubated with stirring for 2 hours at 4° C. The resuspended cells are sonicated for 2 minutes on ice, followed by centrifugation at 12,000×g for 10 minutes and the supernatant is collected and dialyzed overnight against 1 l of urea sodium acetate buffer (8 M urea, 20 mM sodium acetate, pH 5.5) with two changes. After a centrifugation for 20 minutes at 31,000×g, the clear protein supernatant solution (150 ml) is collected and mixed with approximately 25 ml of pre-swollen phosphocellulose (equilibrated 2×in column buffer, P11, Whatman International Ltd., Kent, UK) for 3 hours. The resulting slurry is washed twice with the urea sodium acetate buffer and poured into a column. The column is connected to an FPLC system (Pharmacia) and step washed twice with 140 mM and 210 mM NaCl in the urea sodium acetate buffer. The protein is then eluted using a 0.21 to 0.7 M NaCl linear gradient in the urea sodium acetate buffer. At the end of the salt gradient, the column is maintained at 0.7 M NaCl until all the protein is eluted. Fractions are analyzed by SDS-PAGE and those containing RNase H are pooled and desalted using a Sephadex G-25 column with buffer containing 150 mM NaCl in 20 mM sodium acetate, pH 5.5. The eluted protein fractions are pooled, concentrated with a Centriprep 10 filter (Amicon, Beverly, Mass.), and stored at −20° C. in glycerol storage buffer (40% glycerol, 150 mM NaCl and 20 mM sodium acetate, pH 5.5).

Example 4
Determining Methicillin Resistance Status of *Staphylococcus Aureus* by Detection of MECA Gene Using CPT Reaction The following example demonstrates the utility of chimeric probe mecA945–29 (SEQ ID NO:5) and the effectiveness of spermine and EGTA in CPT reaction for the detection of the mecA gene from crude lysates of *S. aureus* isolates.

This experiment was designed to examine the effect of spermine and EGTA in the CPT reaction for detection of the mecA gene in MRSA isolates using crude lysates.

For this experiment the MRSA (ATCC 33592, American Type Culture Collection, Rockville, Md.) and MSSA (ATCC 11632) isolates were grown on trypticase soy agar (TSA) plates with 5% sheep blood (PML Microbiologics, Richmond, BC) at 37° C. overnight. A sterile swab was used to remove the colonies from the TSA plate followed by resuspension of the cells in 2 ml of 0.05% Triton X-100® in 20 mM TES buffer (pH 6.8). The cell suspensions were then adjusted to McFarland #5 standard cell density (approximately 1.5×10$^7$ cells/ml). Fifty µl of the cell suspensions (approximately 7.5×107 cells) were then transferred to microcentrifuge tubes. Lysis of the cells was carried out with the addition of achromopeptidase (Wako Bioproducts, Richmond, Va.) to a final concentration of 150 units/ml per sample. The suspensions were mixed and incubated at 37° C. for 20 minutes.

The chimeric probe mecA945–29 was synthesized and labeled as described in Examples 1 and 2. Thermostable RNase H was produced as described in Example 3. CPT reactions and analysis were carried out as in Example 2 except for the following: 1.8 fmol mecA945–29 chimeric probe was used and the additive concentrations tested were 1 mM EGTA, 2 mM spermine or a combination of 1 mM EGTA and 2 mM spermine. Fifty µl of crude lysates samples were heat denatured in a heating block at 95° C. for 5 minutes, and then directly transferred to a 58° C. water bath (reaction temperature was 56° C.). The reaction cocktail (50 µl) was immediately added and the incubation was continued for an additional 20 minutes. At the end of incubation, an equal volume of loading dye containing 40 mM PB (100 µl) was added to the samples in the water bath. The samples were then transferred to a 95° C. heating block for 5 minutes. Samples were spun down briefly and 20 µl was loaded onto an acrylamide gel for electrophoresis.

Table 1 summarizes the results of the effect of spermine and EGTA in CPT reactions for detection of the mecA gene from MRSA lysates. Briefly, it was observed that in the absence of spermine or EGTA there was no differentiation between the MRSA and MSSA isolates due to the high C4 background. The addition of EGTA alone reduced the Percent Probe Cut in both MRSA and MSSA, but still did not permit the differentiation between the two. Addition of spermine alone to the CPT reaction permitted the detection of MRSA by lowering C4 background, which resulted in a signal to noise ratio of approximately 5. Addition of both EGTA and spermine into the CPT reaction dramatically improved detection of the target. As shown in Table 1, there was a major reduction in the C4 background and mecA MRSA could be detected with an impressive signal to noise ratio of 20. These results clearly indicate the necessity of adding both spermine and EGTA to the cycling reaction in order to obtain clear differentiation between MRSA and MSSA isolates.

TABLE 1

The effect of spermine and EGTA in CPT reactions for detection of mecA gene from crude lysates of MRSA.

| EGTA (mM) | Spermine (mM) | C4 (MSSA) Background (%) | MRSA Probe Cut (%) | MRSA Net Probe Cut (%) | S:N |
|---|---|---|---|---|---|
| — | — | 84 | 77 | 0 | — |
| 1 | — | 21 | 22 | 1 | 1.0 |
| — | 2 | 15 | 71 | 56 | 4.8 |
| 1 | 2 | 2.5 | 51 | 48 | 20.0 |

The above example demonstrates the successful use of isotopically labeled chimeric mecA945–29 probe for differentiating MRSA from MSSA by the detection of mecA gene in the presence of the additives spermine and EGTA.

Example 5
Clinical Screening for Methicillin Resistant Staphylococcal Isolates by Detection of the MECA Gene using CPT Reaction The following example demonstrates the successful use of isotopically labeled chimeric probe and the additives, spermine and EGTA, in CPT reactions for the detection of mecA gene from crude lysates of staphylococcal clinical isolates.

This experiment examines the use of $^{32}$P labeled chimeric probe mecA945–29 (SEQ ID NO: 5) and the combination of spermine (2.0 mM) and EGTA (1.0 mM) in CPT reaction for the detection of the mecA gene from crude lysates of 285 staphylococcal isolates. These isolates were from the following sources: Wishart Memorial Hospital (Indianapolis, Ind.), Cleveland Clinic Foundation (Cleveland, Ohio), Vancouver General Hospital (Vancouver, BC) and 25 reference strains. In total there were 238 *S. aureus* and 47 *S. epidermidis* isolates.

The crude lysate preparations, probe synthesis, CPT procedure and analyses were carried out as described in Example 4 except that the cells were picked from the TSA blood plate with a 1 µl plastic loop (PML Microbiological, Richmond, BC, Canada) resuspended in 50 µl of 0.05% Triton X-100® in 20 mM TES buffer (pH 6.8) and lysed with the addition of achromopeptidase (Wako Bioproducts) as described in Example 4. The DNA was heat denatured at 95° C. for 5 minutes prior to use. The experiment was carried out as an operator blind study. The isolates were also tested with conventional oxacillin screening agar (PML Microbiological), Kirby-Bauer Disc diffusion, minimal inhibitory concentration (MIC) using E-Test with 4% NaCl Meuller-Hinton and S. aureus were tested with the BBL® Crystal™ MRSA ID test (Beckton Dickinson).

Figure 2:
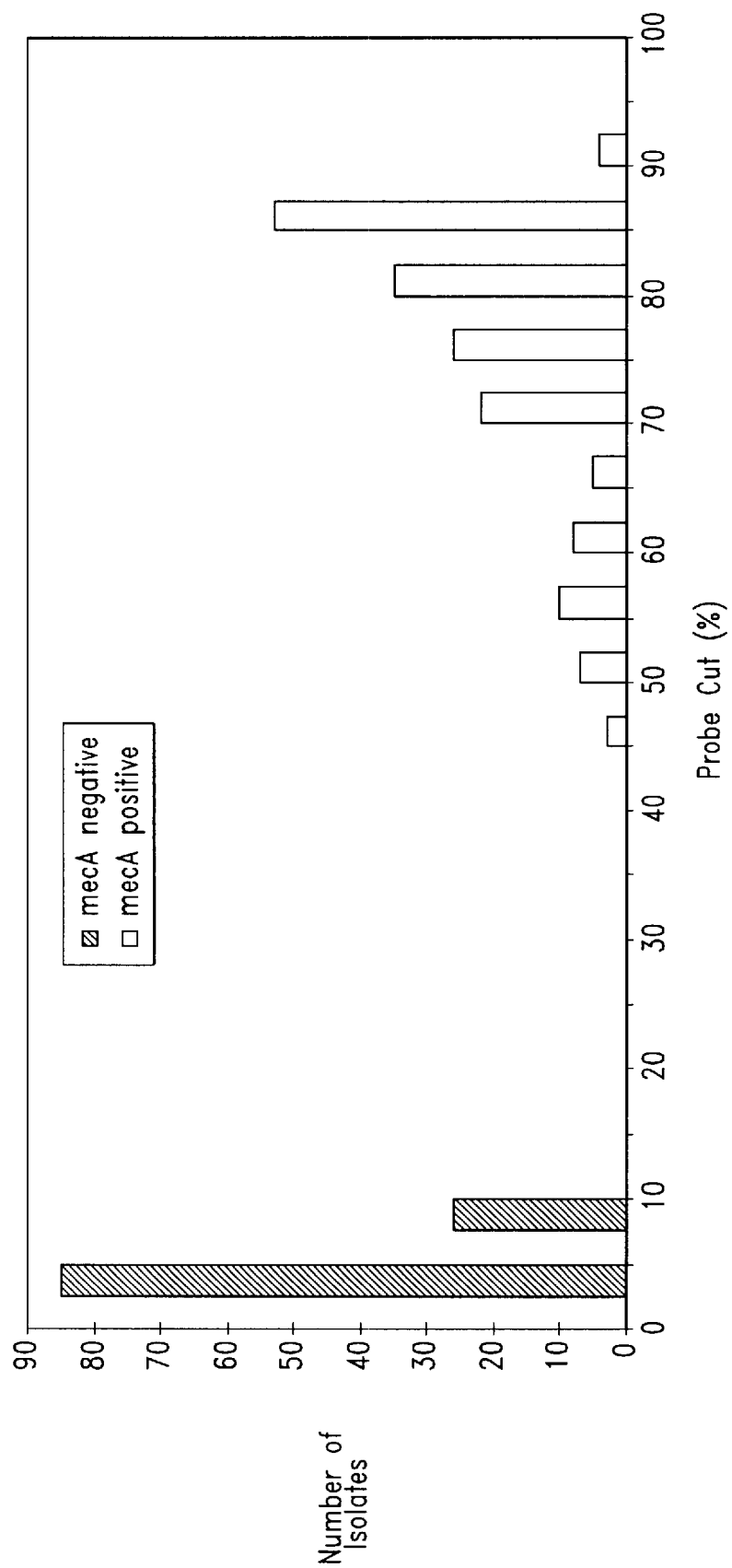
FIG. 2 is a histogram showing the frequency distribution results of screening 285 Staphylococcus isolates, including *S. aureus* and *S. epidermidis*, for the mecA gene from crude lysates using Cycling Probe Technology reaction. The $^{32}P$ labeled chimeric probe was mecA945–29 (SEQ ID NO:6) and the reaction mixture contained the combination of 1.0 mM ethylenebis(oxyethylenitrilo)-tetracetic acid (EGTA) and 2.0 mM spermine. The isolates can be divided into mecA positive or mecA negative based on the Percent Probe Cut.

When CPT reaction results were compared to oxacillin agar screening, 4 discrepant samples were found. These isolates were observed to be agar screen positive but CPT negative. After discrepant resolution by PCR (Example 7) it was confirmed that the mecA gene was absent in these isolates. The results of the above experiment are depicted in FIG. 2 as a frequency distribution histogram of the number of isolates versus Percent Probe Cut. Briefly, the frequency distribution of Percent Probe Cut separated the isolates into two distinct populations based on presence or absence of mecA gene using operator blind study.

Each of the susceptibility tests employed in this study failed to correctly identify several isolates of staphylococci. The gold standard oxacillin agar screen identified 4 S. aureus isolates as MRSA, although the mecA gene was shown not to be present. Each of these four isolates displayed borderline resistance to oxacillin (MIC's 3–16 ug/ml) and were likewise misidentified by MIC E test and oxacillin disk diffusion. One of these four isolates was further misidentified by the BBL Crystal ID MRSA System. An additional 31 S. aureus isolates lacking the mecA gene were designated as MRSA by the E test with oxacillin MIC's 3–12 ug/ml and two of these isolates were also missed by oxacillin disk diffusion. Each of these borderline oxacillin resistant S. aureus (BORSA) isolates were further shown to be susceptible to oxacillin in the presence of clavulanic acid by disk diffusion.

Conventional susceptibility tests cannot reliably differentiate between oxacillin borderline-susceptible S. aureus isolates and heterogeneously resistant MRSA isolates with low MIC.

TABLE 2

Isolates incorrectly identified by susceptibility tests

| | Isolates | | |
|---|---|---|---|
| | BORSA | MRSA | MRSE[1] |
| Total Isolates Tested | 35 | 127 | 46 |
| MIC E-Test | 35 | 0 | 4 |
| Oxacillin Agar Screen | 4 | 0 | 0 |
| Crystal MRSA ID | 1 | 4 | Not Done |
| Oxacillin Disc Diffusion | 6 | 4 | 2 |

[1]MRSE refers to methicillin resistant *Staphylococcus epidermidis*

The CPT assay accurately detected the mecA gene in S. aureus and S. epidermidis isolates and allowed for the correct identification of methicillin resistant staphylococci from methicillin susceptible staphylococci. This assay was also able to differentiate the mecA positive MRSA from BORSA, which does not contain the mecA gene.

The above example demonstrates the sensitivity and specificity of the isotopically labeled mecA945–29 probe for the mecA gene from crude lysates of both coagulase positive and negative staphylococcal clinical isolates.

Example 6
PCR Detection of MECA Gene

PCR for discrepant analysis is carried out by the following method.

Oligonucleotide primer pair mecA834–25 and mecAL1039–22 (SEQ ID NOs:9 and 10), specific for the mecA sequence of MRSA, were synthesized as described in Example 1. Crude lysates of MRSA and MSSA ATCC isolates were used as controls and PCR was performed after the hot start with the Taq polymerase.

Hot-start PCR was carried out in a 50 µl volume by adding the Taq polymerase at 80° C. after denaturation for 5 minutes at 95° C. The final PCR reaction mixture contained the following: 200 µM of each dNTP mix (dATP, dGTP, dCTP, dTTP, Pharmacia), 1.5 mM of $MgCl_2$, 50 mM KCl, 20 mM Tris HCl, pH 8.4, (1×PCR buffer, Gibco-BRL), 0.5 µM of each primer pair, 1U of Taq DNA polymerase (Gibco-BRL) and 2 ng of Staphylococcus DNA crude lysate sample in a final reaction volume of 50 µl. Samples were cycled in the thermal cycler (PTC 100, MJ Research Inc.) using a cycle of 94° C. for 40 seconds, 53° C. for 40 seconds and 72° C. for 90 seconds. Amplification is carried out for 50 cycles.

After amplification the samples were analyzed electrophoretically using 1.8% agarose gel containing 0.5 µg/ml of ethidium bromide. A molecular weight marker was also included. The sample was considered to be positive if the 227 bp amplicon was detected. This amplicon was detected in the ATCC MRSA control but not in the ATCC MSSA control or any of the discrepant S. aureus isolates.

Example 7
Non-sotopic MRSA Assay

The following example demonstrates a rapid non-isotopic CPT assay for the detection of mecA gene in clinical isolates of S. aureus.

Figure 3:
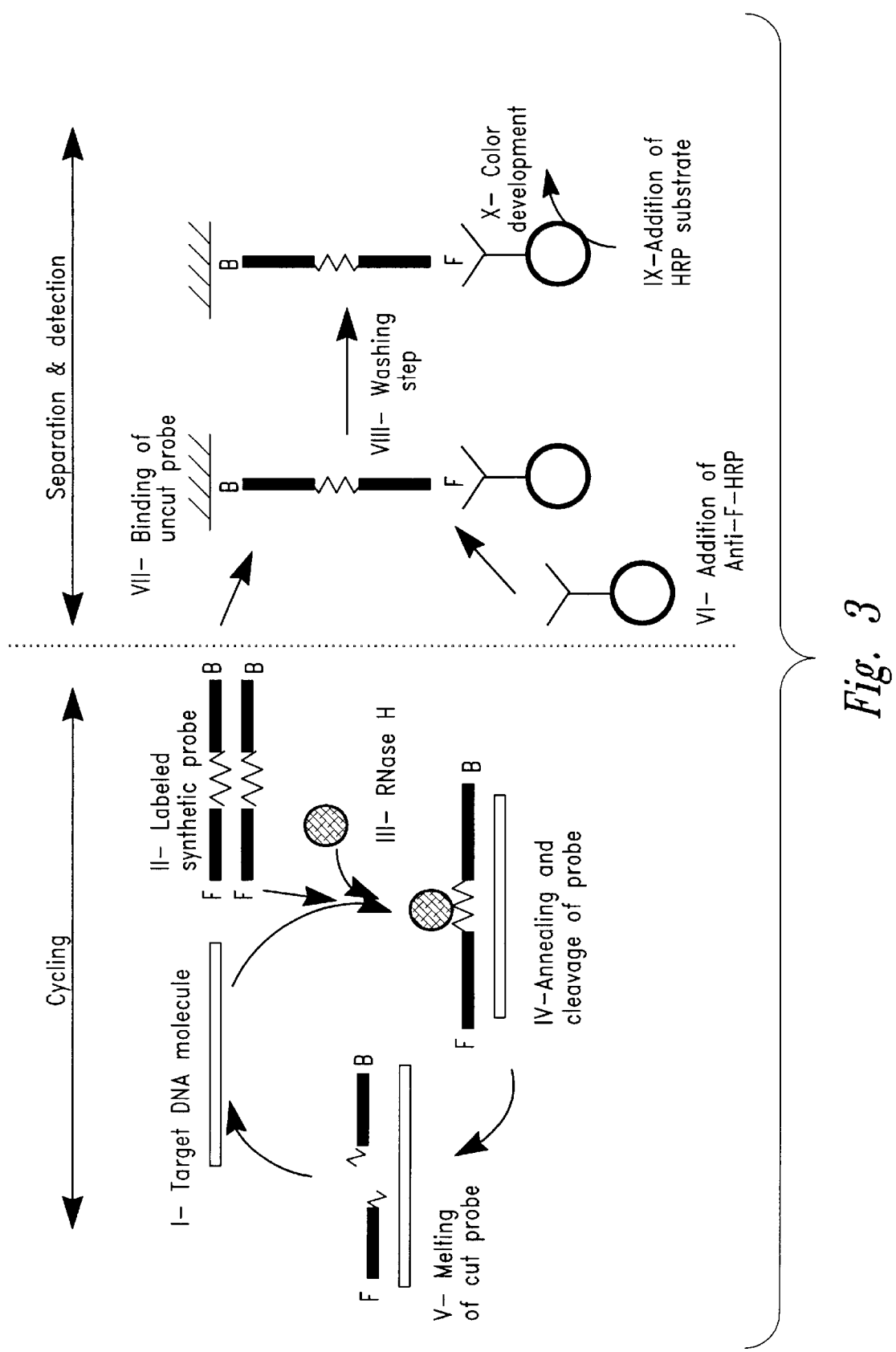
FIG. 3 is a schematic illustration of the Non-Isotopic CPT Assay. Single-stranded target (I) serves as a catalyst for CPT. In the presence of probe (F-DNA-RNA-DNA-B) (II) and RNase H (III), the RNA portion of the probe-target complex (IV) is cleaved by RNase H. The shorter cleaved probe fragments dissociate from the target thereby regenerating the target DNA for further cycling (V). The anti-fluorescein antibody coupled to horse radish peroxidase (anti-F-HRP) is added (VI) and the reaction is transferred to streptavidin coated plates. The uncut probe bound to anti-F-HRP is captured using the plates (VII). Excess antibody is washed (VIII) and the HRP substrate is added (IX) to measure the amount of uncleaved probe. The absorbance, or color development (X), is inversely proportional to the amount of target DNA.

The non-isotopic MRSA Assay which combines CPT with an enzyme immunoassay (CPT-EIA) is schematically illustrated in FIG. 3. This Rapid MRSA Test uses a fluoresceinated and biotinylated chimeric probe which provides an RNase H sensitive scissile linkage when bound to the complementary base sequence of the mecA gene. The uncleaved probe (mecA negative) is detected by binding of the probe to a solid surface and attachment of an antibody conjugated with horse radish peroxidase, which converts a substrate to a colored end product. Cleavage of the probe (mecA positive) prevents binding of the probe-antibody complex to the solid surface thus preventing formation of the colored end product. A result is generated in 90 minutes.

This experiment examines the use of fluorescein labeled chimeric probe FmecA945–29B (SEQ ID NO: 5) and the combination of spermine and EGTA in CPT reaction for the detection of the mecA gene from crude lysates of 102 staphylococcal isolates. The source of S. aureus isolates were from the following: Wishard Memorial Hospital, Cleveland Clinic Foundation, Vancouver General Hospital and ATCC. In total there were 51 MRSA and 51 MSSA isolates.

Effective lysis of both MRSA and MSSA were developed and optimized. The composition of the Lysis Reagent is as follows: 200 Units/ml of achromopeptidase (Wako Bioproducts, Wako), 0.02 mg/ml lysostaphin (Sigma, St. Louis, Mo.), 0.05% (v/v) Triton X 100® and 20 mM TES buffer, pH 8.5.

The chimeric probe FmecA945–29B was synthesized, fluoresceinated and biotinylated as described in Example 1. The purified thermostable RNase H was prepared as described in Example 3. The isolates were grown as described in Example 4 and 1 µl loopful of culture growth was placed in 1.5 ml microcentrifuge tube containing 50 μL of the Lysis Reagent. The samples were incubated at 54° C. or room temperature for 10 minutes. DNA was denatured at 95° C. for 2 minutes prior to CPT reaction. The optimized CPT reaction reagents for the subtractive assay were as follows: 20 fmol/reaction of FmecA 945–29B, 50 μl of crude lysate, 0.05% Triton X 100®, 2 mM $MgCl_2$, 25 μM EDTA, 625 μM spermine, 1.65 μg/reaction of RNase H, 20 mM TES, pH 6.8, in final reaction volume of 100 μl. The controls used were mecA positive *S. aureus* (ATCC 33592) and mecA negative *S. aureus* (ATCC 11632). CPT reaction was carried out at 54° C. for 25 minutes.

After cycling, 100 μl of Binding Reagent (Peroxidase Stabilizing Buffer, DAKO, Mississauga, ON), sheep polyclonal anti-fluorescein-horse radish peroxidase conjugated antibody (1/750 dilution, NEN, Boston, Mass.) was added to the tubes. Detection was carried out using streptavidin coated strip wells (Boehringer Mannheim GmbH, Germany, Boeringer). The CPT reaction was transferred to streptavidin coated strip well, mixed for 10 seconds and incubated for 10 minutes at room temperature. The liquid was discarded and washed twice with 300 μl of Wash Buffer (137 mM NaCl, 2.7 mM KCl, 1.8 mM $KH_2PO_4$, 10.1 mM $Na_2HPO_4$, 0.5% Tween 20, pH of 7.3). This was followed by addition of 200 μl of substrate (Tetramethylbenzidine/$H_2O_2$, Sigma) and allowed to develop for 3 minutes at room temperature. The development was stopped using 100 μl of Detection Stop Reagent (750 mM Tris, 1.5% (w/v) sodium dodecyl sulfate, pH of 7.7). The plate is read using a Vmax plate reader (Molecular Devices) set at OD of 650 nm ($OD_{650}$).

Figure 4:
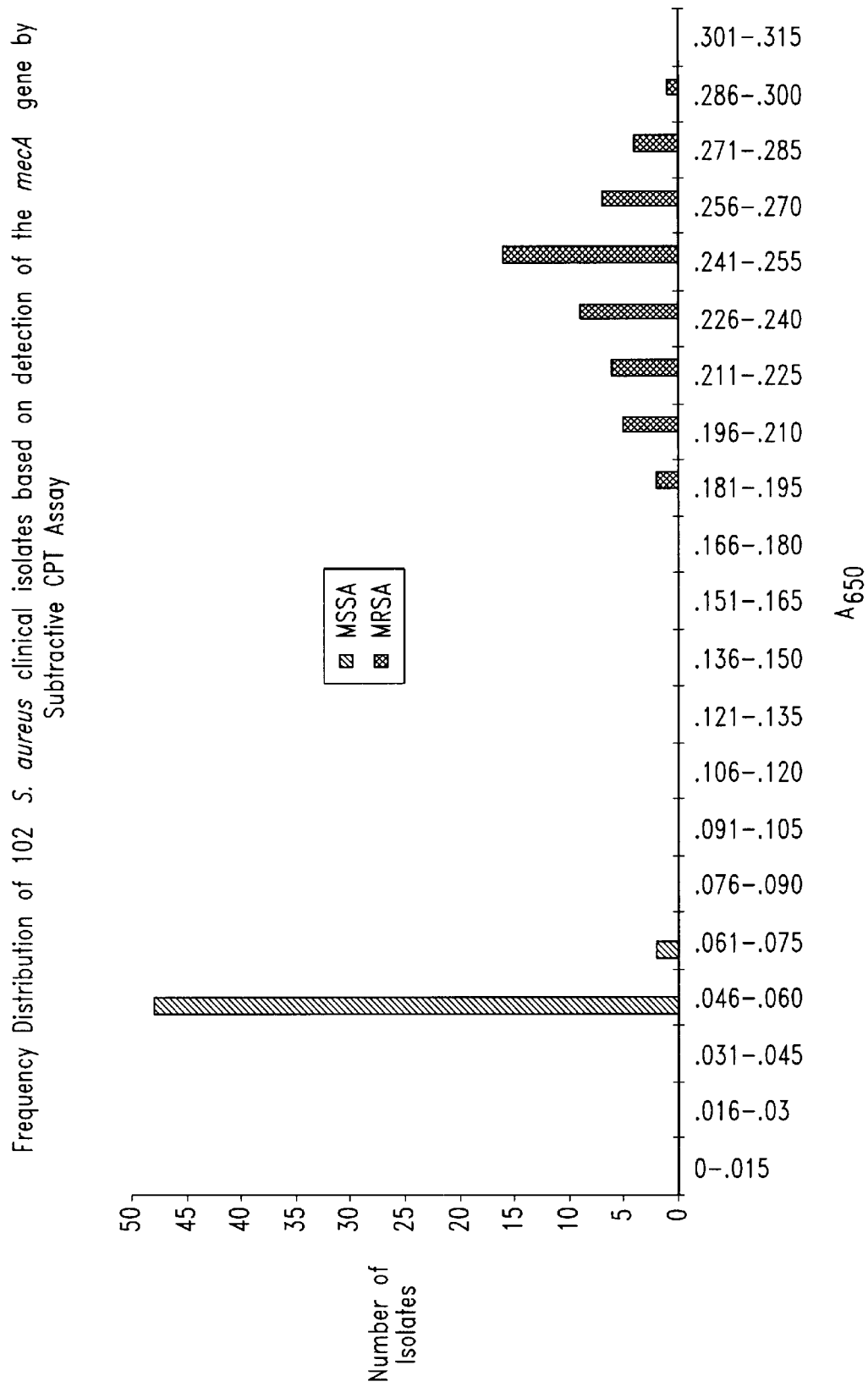
FIG. 4 is a histogram showing the frequency distribution of 120 *S. aureus* clinical isolates based on the detection of the mecA gene by Non-isotipic CPT Assay using the fluoresceinated and biotinylated chimeric probe FmecA945–29B (SEQ ID NO:5). The assay was carried out on crude lysates and the isolates can be differentiated into MRSA (mecA positive) and MSSA (mecA negative) as two non-overlapping populations based on the absorbance value at 650 nm ($A_{650}$).

Table 3 and FIG. 4 summarize the results of the screen for the mecA gene of MRSA by using the subtractive CPT assay.

TABLE 3

The mean and standard deviations (SD) of absorbance at 650 nm ($A_{650}$) from the experiment examining the detection of MRSA (n = 51) and MSSA (n = 51) clinical isolate lysates using the subtractive CPT assays.

| n | MRSA 51 | MSSA 51 |
|---|---|---|
| $A_{650\ nm}$ Mean | 0.053 | 0.239 |
| Standard Deviation | 0.004 | 0.024 |
| Mean − 3x SD | 0.040 | 0.166 |
| Mean + 3x SD | 0.066 | 0.314 |

The results indicate that all 51 MRSA or MSSA data points lie within 3 standard deviations (SD) of their corresponding means. Therefore no overlap exists between the MRSA mean plus 3×SD and the MSSA mean minus 3×SD. This allowed for an unambiguous test results which separates the MRSA population from the MSSA population.

The above example demonstrates that the chimeric fluoresceinated and biotinylated mecA945–29 probe can successfully be used in a non-isotopic CPT-EIA for differentiating MRSA from MSSA by detecting the mecA gene.

Example 8

MRSA Test: Format, Reagent and Kit Composition

The following is one representative example of a kit for detecting the mecA gene from MRSA.

This kit allows for rapid detection of MRSA by detecting the mecA gene using the non-isotopic CPT assay (CPT-EIA) and has been optimized to detect MRSA isolates (discrepants) that are hard to lyse or those that produce nucleases.

The Rapid MRSA Test Kit (48 tests) is composed of the following items:
MRSA Lysis Reagent (2)
Streptavidin Coated Microwells (48)
MRSA Cycle Reagent (48)
Wash Buffer (1×50 mL)
MRSA Lysis Reconstitution Buffer (1×3 mL)
Detection Substrate Reagent (1×12 mL)
Cycle Reconstitution Buffer (1×6 mL)
Detection Stop Reagent (1×5.5 mL)
MRSA Cycle Stop Reagent (1×6.8 mL)
Transfer Pipette (50)
50 μL Dropstira (75)
50 μL Dropstira (75)
200 μL Dropstir (50)
200 μL Dropstir (50)

The following describes the composition, reagents and materials that form part of the kit:

MRSA Lysis Reconstitution Buffer: Water and 20 ppm ProClin 300™ (Sigma).

MRSA Lysis Reagent (lyopholized): TES, Triton X-100® Trehalose (Sigma), Achromopeptidase (Wako) and EGTA Cycle Reconstitution Buffer: 4 mM $MgCl_2$ and 20 ppm ProClin 300™.

MRSA Cycle Reagent (lyopholized): Trehalose, Polyvinylpyrrolidone, TES, Triton X-100® spermine, mecA probe, RNase H and bovine serum albumin.

MRSA Cycle Stop Reagent: Buffered Salt Solution (DAKO) containing anti-fluorescein antibody conjugated with horse radish peroxidase (1/1000 final dilution).

Streptavidin Coated Microwell (Boehringer).

Wash Buffer: 137 mM NaCl, 2.7 mM KCl, 1.8 mM $KH_2PO_4$, 10.1 mM $Na_2HPO_4$, 0.5% Tween 20 and 20 ppm ProClin 300.

Detection Substrate Reagent: Tetramethylbenzidine (Sigma) and $H_2O_2$.

Detection Stop Reagent: 0.75 mM Tris and 1.5% Sodium dodecyl sulfate.

The procedure for carrying out the assay for detecting the mecA gene from the crude lysates of *S. aureus* is as follows:
A. Reconstitution of MRSA Lysis Reagent
  1. To a vial of MRSA Lysis Reagent pipette 1.5 mL of MRSA Lysis Reconstitution Buffer.
  2. Swirl to dissolve.
  3. Let sit at room temperature for 2 to 3 minutes before use.
  4. Once reconstituted a vial of MRSA Lysis Reagent can be used for 2 weeks when stored at 2°–8° C.
B Reconstitution of MRSA Cycle Reagent 1. The reconstitution should be performed during the incubation steps of Specimen Preparation. 2. To a vial of MRSA Cycle Reagent add 2 drops of the Cycle Reconstitution Buffer. 3. Swirl to dissolve. 4. This is a single use reagent. This reagent must be used within 30 minutes of reconstitution.
C Sample Preparation 1. Using a 50 μL Dropstir add one drop of the reconstituted MRSA Lysis Reagent to each 1.5 mL microcentrifuge tube. (one tube per sample) 2. Add 1 μL loop of growth from an 18 to 24 hour culture on a tryptic soy agar plate containing 5% sheep blood. Mix well to completely suspend cell growth. 3. Place at 55° C. for 20 minutes. 4. Place at 95° C. for 5 minutes.
D Cycling Probe Technology 1. Transfer tubes with lysate to 55° C. 2. Using a 50 μL Dropstir add one drop of the reconstituted MRSA Cycle Reagent to each tube. 3. Incubate at 55° C. for 25 minutes. 4. Add 3 drops of MRSA Cycle Stop Reagent, with tubes at 55° C.

E Detection 1. Place the necessary number of Streptavidin Coated Microwells (one Microwell per sample) into the Microwell frame. 2. Transfer the entire cycle reaction to Streptavidin Coated Microwell using a transfer pipette. 3. Incubate at room temperature for 10 minutes. 4. Invert Streptavidin Coated Microwell to discard liquid. 5. Fill each Streptavidin Coated Microwell completely with Wash Buffer. 6. Invert Streptavidin Coated Microwell to discard liquid. 7. Tap each Streptavidin Coated Microwell 5 times on dry paper towel. 8. Repeat steps 5–7. 9. Using a 200 $\mu$L Dropstir add one drop of Detection Substrate Reagent to each of the Streptavidin Coated Microwells. 10. Place at room temperature for 5 minutes. 11. Add 4 drops of Detection Stop Reagent to each Streptavidin Coated Microwell. 12. Mix for 10 seconds. 13. Incubate at room temperature for 3 minutes. 14. Within 30 minutes visually read and record the color zone or measure/record the $OD_{650}$.

Example 9

Direct Fluorescence CPT Assay For MECAMRSA

The following example demonstrates the use of a direct fluorescence assay for the detection of the mecA gene in MRSA isolates by CPT using crude lysates.

Two experiments were carried out for the detection of the mecA gene from clinical isolates using the direct fluorescence assay (DFA) combined with CPT (CPT-DFA). In the first experiment, 58 isolates were screened using a plate reader format, and in the second experiment, 120 isolates were screened using single tube reader format. Briefly, the assay uses a fluoresceinated and biotinylated chimeric probe complementary to a sequence within the mecA gene present in MRSA, but not in MSSA. The probe is labeled with fluorescein at the 5' end and biotin at the 3' end. The CPT assay is performed with crude lysate preparations from Staphylococcal cells in the presence of RNase H and the chimeric probe. After the cycling reaction, streptavidin coated magnetic beads are added to bind the uncleaved probe. The supernatant containing the cleaved fragment labeled with fluorescein is separated from the beads using a magnet and the supernatant is transferred to a glass tube or a microtiter plate for fluorescence measurement.

A. Source of Clinical Isolates and Sample Preparation

The source of the fifty-eight clinical isolates were obtained from Cleveland Hospital, Wishard Memorial and Vancouver General Hospital. All MRSA and MSSA cells were prepared and lysed essentially as described in Example 4 except that the lysates were prepared as either 2×McFarland No. 5 standard density or 1 $\mu$l loop of cells in 50 $\mu$l volume. One $\mu$l loop of cells is approximately equivalent to 5×McFarland No. 5 standard.

B. Binding of Biotinvlated Probes using Streptavidin Coated Magnetic Beads

The streptavidin coated magnetic beads (Dynal M-280, Oslo, Norway) were prepared by washing two times in an equal volume of TES cycling buffer (4 mM $MgCl_2$, 0.05% Triton X-100®, 20 mM TES, pH 6.8). The beads were then re-suspended in 10 times the original volume with cycling buffer containing NaCl. The diluted beads were added to the reactions containing biotinylated probe to a final concentration of 50 $\mu$g of beads/reaction and a final NaCl concentration of 1.5 M. Binding was carried out in a thermomixer (Eppendorf) at 37° C. with mixing at a speed of 13×100 minutes$^-$, for 10 minutes. The supernatant was then separated from the beads using an MPC magnet (Dynal).

C. Fluorescence Detection of Probe after Binding

Probe was detected after binding using the Fluoroskan fluorescence plate reader (Labsystems, Needham. Mass.) by placing the supernatant containing the cleaved probe in a well of MicroFluor 'U' black round bottom plate (Dynatech, Chantilly, Va.). To each well containing a sample, 150 $\mu$l of 0.22 M DEA pH 10 was added. Any bubbles in the wells were removed using the edge of a Kimwipe (Roswell, Ga.). The plate was scanned in the plate reader with an excitation wavelength of 485 nm, an emission wavelength of 538 nm and a scan/well time of 20×0.1 sec, at room temperature. Similar detection using the Beacon-2000 tube reader (Panvera, Madison, Wis.) was performed, by placing the supernatant containing the probe in a borosilicate glass tube (Kimble, Toledo, Ohio), that contains 11 $\mu$l of 2.0 M DEA, pH 10. The samples were then vortexed and the fluorescence intensity was measured using the static mode of the Beacon-2000 instrument. The excitation and emission wavelengths were 485 nm and 515 nm respectively and an average of 10 read cycles at 25° C. was used.

D. CPT Procedure with Crude Lysates of MRSA or MSSA

The assay used a chimeric probe FmecA945–29$(XL)_4B_3$ (SEQ ID NO:5) labeled with fluorescein at the 5' end and three biotin at the 3' end. Cycling reactions with crude lysate were performed in a 50 PI reaction containing 25 $\mu$l of crude lysates. The lysates were denatured at 95° C. for 2 minutes. CPT reaction was carried out and the final conditions were as follows: 1 pmol chimeric probe, 25 $\mu$l of crude lysates, 50 $\mu$M EDTA, 0.5 mM spermine, 1.5 $\mu$g of RNase H in a final reaction volume of 50 $\mu$l. All reactions were cycled in a 60° C. water bath, in microcentrifuge tubes (uncapped) for 50 minutes. Reactions were stopped with the addition of an equal volume of diluted beads (50 $\mu$g of beads/reaction in Cycling Buffer and NaCl), while still in the water bath. Binding and detection were carried out as described above. The net relative fluorescence units (RFU) is calculated as the difference between the fluorescence intensities of MRSA and MSSA.

Figure 5:
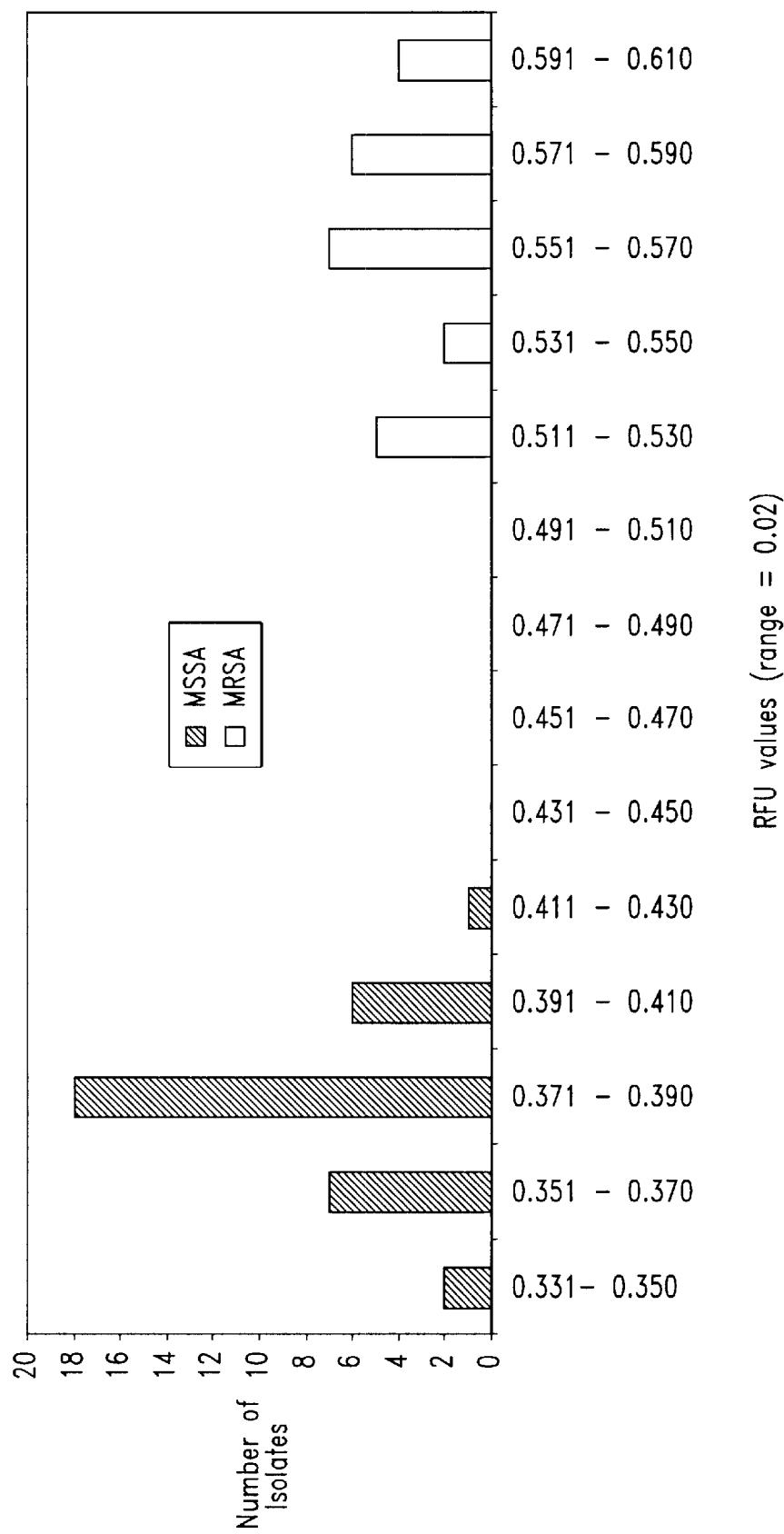
FIG. 5 is a histogram showing the frequency distribution of 58 *S. cureus* clinical isolates based on the detection of the mecA gene by CPT Direct Fluorescence Assay using the fluoresceinated and biotinylated chimeric probe using the plate format. The chimeric probe was FmecA945–29(XL)$_4$B$_3$(SEQ ID NO:5) and the CPT assay was carried out on crude lysates. The isolates can be differentiated into MRSA (meca positive) and MSSA (mecA negative) as two non-overlapping populations based on relative fluorescence units (RFU).

The Fluoroskan plate reader was used to measure the fluorescence in the initial clinical screen of 58 isolates. These results are summarized in FIG. 5 as a frequency distribution histogram. Briefly, these results show that the MRSA and MSSA isolates could easily be differentiated as two non-overlapping populations and it was concluded that the assay had 100% sensitivity and 100% specificity for detection of the mecA gene relative to culture and PCR resolution (see Example 5).

Figure 6:
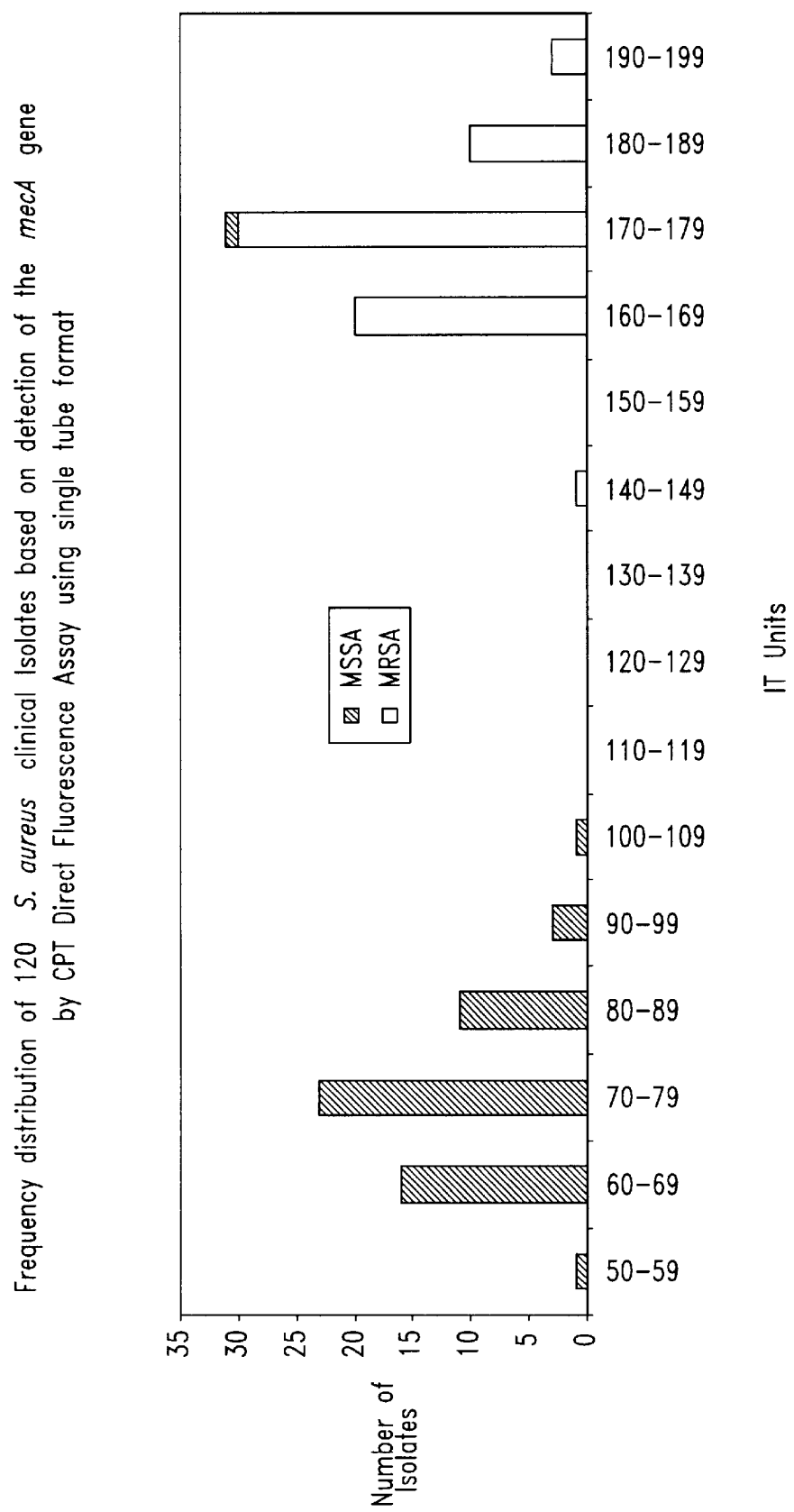
FIG. 6 is a histogram of the results of fluorescence intensities obtained by CPT Direct Fluorescence Assay from a blind screen of 120 clinical *Staphylococcus aureus* isolates for the mecA gene using the single tube format. The chimeric probe was FmecA945–29(XL)$_4$B$_3$ (SEQ4 ID NO:5), the CPT assay was carried out on crude lysates as described in Example 8. These results show that the MRSA and MSSA isolates can easily be differentiated as two non-overlapping populations based on RFU.

In a subsequent assay, *S. aureus* isolates (either MSSA or MRSA), were assayed by the DFA using 1 pmol of probe, with the Beacon-2000 tube fluorometer. The screening results of 120 isolates using the Beacon-2000 are shown in FIG. 6. The range of MSSA samples are 58.1–101.7 RFU and the range of MRSA samples are 144.2–191.9, with a net gap between the highest MSSA sample and the lowest MRSA of 42.5 RFU. In this screen, one susceptible isolate was mis-identified as a resistant isolate, giving 100% sensitivity and 98% specificity. This mis-identification was due to incomplete lysis of an MSSA sample. This strain was correctly identified when it was re-tested using a longer lysis time (data not shown).

The above example demonstrates that the mecA945–29 probe sequence is very specific and sensitive for detection of mecA gene of staphylococci species in crude lysates using the direct CPT fluorescence assay.

Example 10

The following example demonstrates the utility of CPT for rapid detection of PCR amplicons after a low number of PCR cycles.

Figure 7:
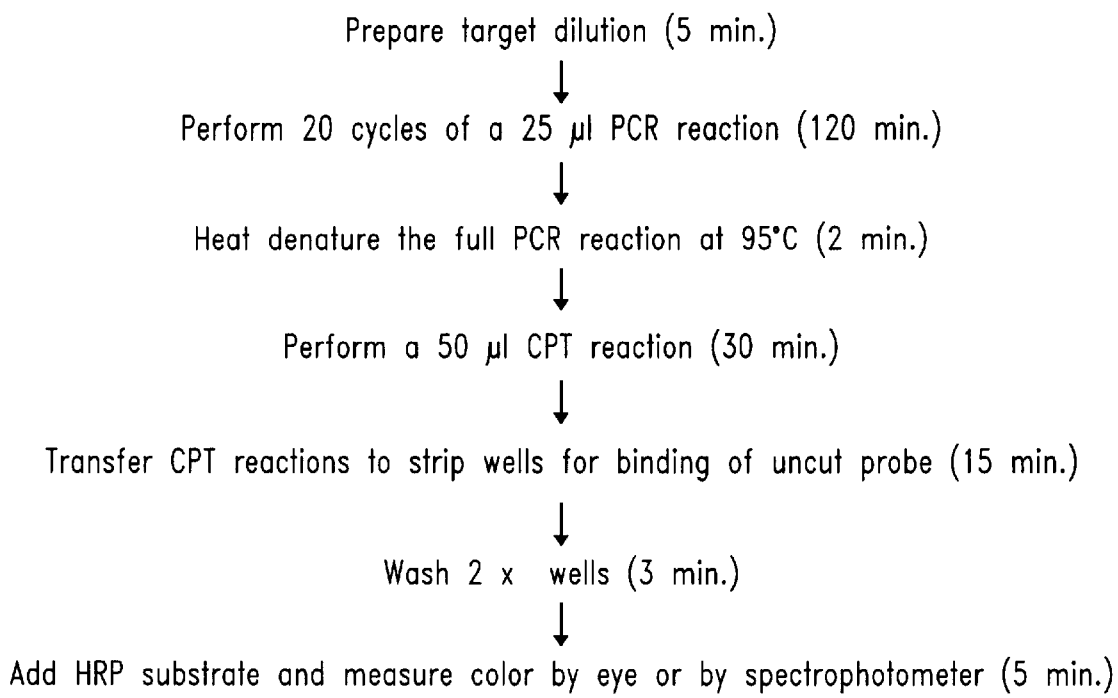
FIG. 7 is a flow chart for carrying out one embodiment for detecting PCR amplicons by CPT.

The mecA gene from MRSA was used as a model system. Initially PCR is carried out and then followed by CPT and detection is carried out by an enzyme immunoassay (CPT-EIA). The CPT-EIA assay has been described previously in Example 7 and illustrated in FIG. 3. The procedure for amplicon detection by CPT-EIA is summarized in FIG. 7.

Crude lysates of MSSA (ATCC 11632) and MRSA (ATCC 33592) strains were grown overnight at 37° C. on tryptic soy agar with 5% sheep blood (PML Microbiologicals, Tualatin, Oreg.). A cell suspension was made in TES buffer (20 mM TES (pH 6.8), 0.05% Triton X-100) to obtain a cell density equivalent to a 5×McFarland#5 standard of turbidity ($7.5 \times 10^9$ cells/ml). The cells were lysed with 150 U/ml achromopeptidase (Wako) for 25 min at 37° C. After lysis, the cells were stored at −20° C. Adequate dilutions were made in deionized sterile water.

The PCR reaction was carried out in a 25 μl reaction containing 20 mM Tris,(pH 8.3) 1.5 MM $MgCl_2$ 0.2 mM dNTPs (Pharmacia), 6.25 pmol of each primer (Table 1) and 0.5 U AmpliTaq Gold (Perkin Elmer). The PTC-100 Programmable Thermal Cycler (MJ Research, Inc.) was used with the following PCR program: 95° C. for 10 min., 20×(94° C. for 40 s, 53° C. for 40 s and 72° C. for 1.5 min). The reaction was submitted to a final extension step at 72° C. for 5 min. and then held at 4° C. prior to analysis. PCR reactions were analyzed by CPT as described below or using a 2% agarose gel and ethidium bromide (Et-Br) staining.

The 227 bp mecA PCR product was used as a standard to determine the sensitivity of CPT-EIA and Et-Br stained gels. The amplicon was prepared as follows: several 100 μl reactions were subjected to 30 cycle PCR and the amplicon was purified using a Qiagen PCR purification kit as recommended by the manufacturer. The 227 bp product was quantified by spectrometer and used as a standard.

The amount of amplicon products was estimated using the following formula: $N=N_0(1+E)^n$ where N is the number of amplicon molecules, $N_0$ is the starting amount of target molecules, n is the number of cycles and E is the PCR efficiency.

TABLE 4

PCR primers and CPT probe sequences. The letters indicate: uppercase is DNA, lower case is RNA, F is fluorescein and B is biotin.

| Name | SEQ ID NO. | Sequence 5' to 3' |
| --- | --- | --- |
| mecA834-25 | 9 | TGGTAAAAAGGGACTCGAAAAACTT |
| mecAL1039-22 | 10 | GGTGGATAGCAGTACCTGAGCC |
| FmecA945-29B | 5 | F-AATAGAGAAAAAGaaaaAAGATGGCAAAG-B |

CPT-EIA. The 25 μl PCR reaction was heat denatured at 95° C. for 2 min and then placed at 54° C. The CPT components in 25 μl were added to the PCR reaction to give a CPT reaction volume of 50 μl. In addition to the PCR components, the reaction contained: 20 mM TES, pH 6.8, 4 mM $MgCl_2$, 0.05%, Triton X-100, 1 mM EGTA, 1 mM Spermine, 10 fmol FmecA945-29B probe (Table 4) and 1.42 μg RNase H. The CPT reaction was incubated at 54° C. for 30 min. and stopped with 100 μl of binding reagent containing 1/600 dilution of anti-fluorescein-HRP (NEN, Boston, Mass.) conjugate in Peroxidase Stabilizing Buffer (DAKO, Mississauga, ON).

After removal from 54° C., the samples were allowed to cool for 3 minutes at room temperature. The samples were then transferred to streptavidin coated strip well (Boehringer Mannheim) and incubated at room temperature for 10 min. with shaking. The wells were washed 2× with wash buffer (137 mM NaCl, 2.7mM KCl, 1.8 mM $KH_2PO_4$, 10.1 mM $Na_2HPO_4$, 0.5% Tween 20, 20 ppm ProClin 300, pH7.3)) and then 200 μl of Single Component TMB Peroxidase EIA substrate (Biorad, Hercules, Calif.) was added. After 3 minutes, color development was halted using detection stop reagent (750 mM Tris, 1.5% SDS, 20 ppm ProClin 300, pH 7.7) and the plates were read at OD 650 nm using a Vmax spectrophotometer (Molecular Devices, Sunnyvale, Calif.) The net $OD_{650}$ (=$OD_{control}-OD_{sample}$) was used to characterize the presence of specific target. The number of times the target is cycled (T) was estimated as follows:

T=# molecules cleaved/number of target molecules.

Figure 8A:
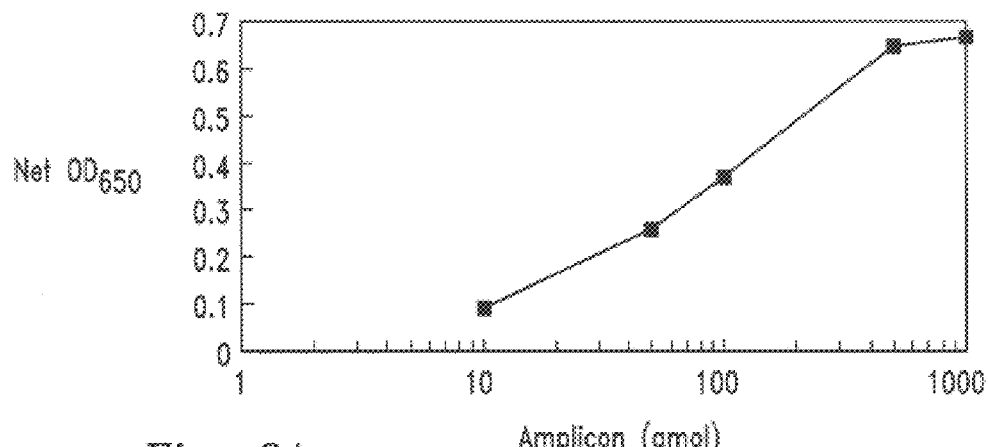
FIG. 8 shows the results for comparison of CPT-Enzyme immunoassay (CPT-EIA, 8A) and Et-Br stained agarose gel (8B) for the detection of PCR amplicon standard.
Figure 8B:
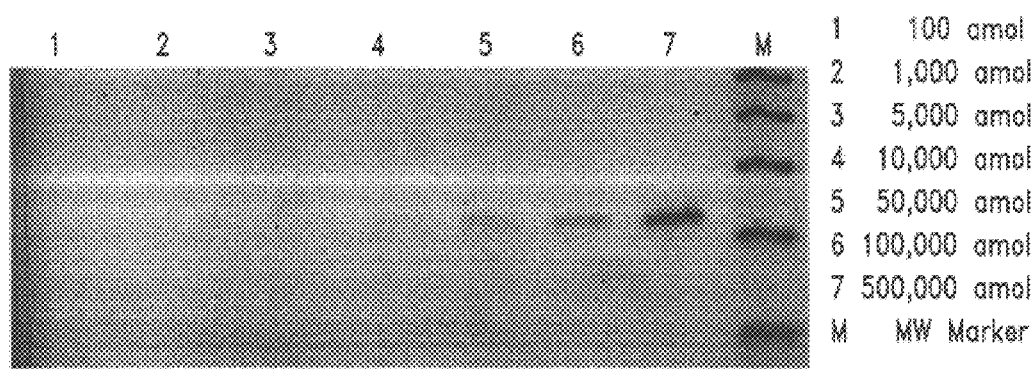

It was found that the detection sensitivity of CPT-EIA using the standard mecA 227 bp amplicon was 50 amol or 7.6 pg (FIG. 8A?). Using the same amplicon, the limit of detection using Et-Br stained agarose gel was 50,000 amol or 7.6 ng (FIG. 8B?). The sensitivity of CPT EIA detection was therefore 3 logs better than that of Et-BR detection. Furthermore, it took approximately 1 hour to analyze the standard amplicons by CPT-EIA compared to 1.5 hours for the analysis by gel. The analysis by CPT-EIA is semi-quantitative whereas the analysis by gel is qualitative.

Figure 9A:
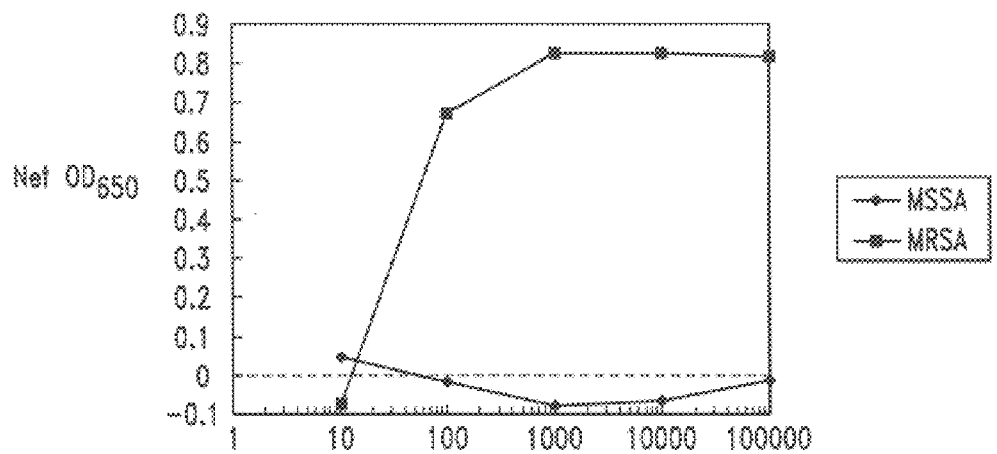
FIG. 9 shows the comparison of sensitivity of the PCR CPT-EIA (9A) to the Ethidium Bromide stained gels (9B) for the detection of the mecA gene from MRSA and MSSA.
Figure 9B:
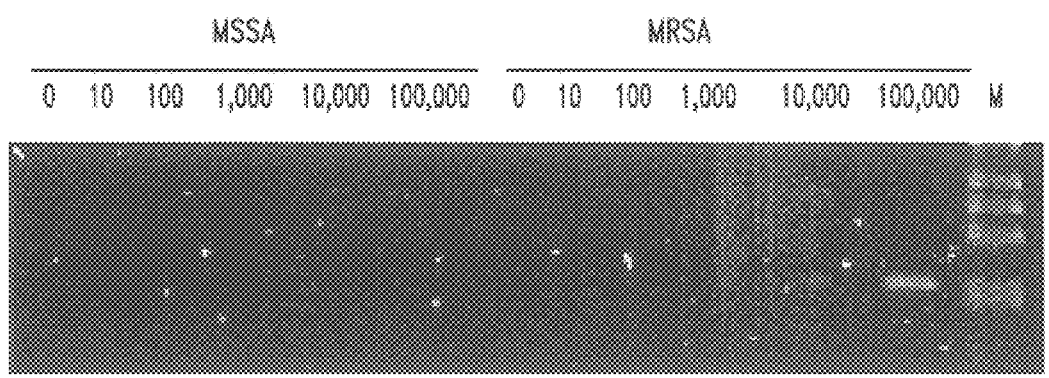
Figure 10A:
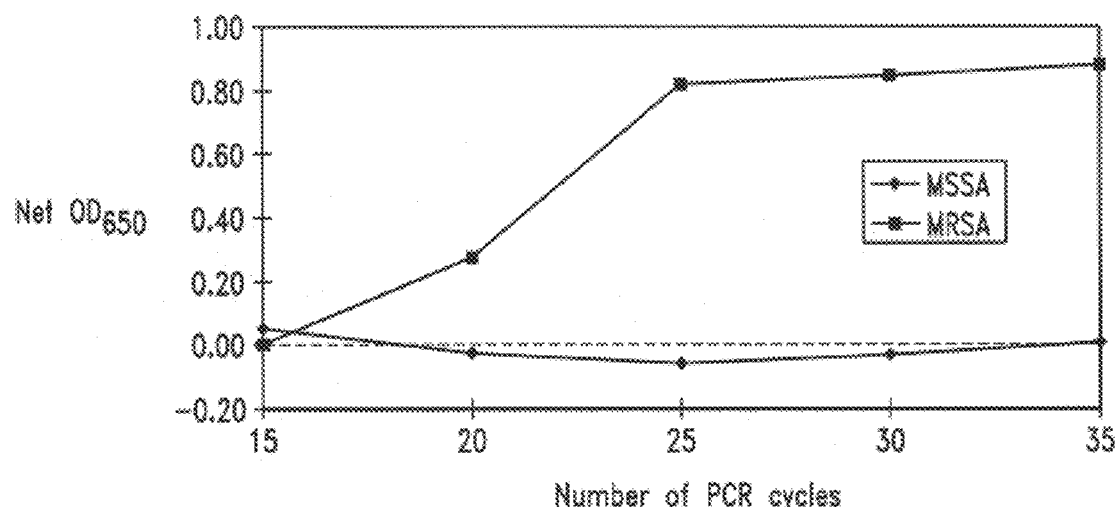
FIG. 10 shows the results of the effect of PCR cycle numbers on the detection by CPT-EIA (IOA) and Ethidium Bromide stained agarose gel(10B) for the detection of the mecA gene from MRSA and MSSA.
Figure 10B:
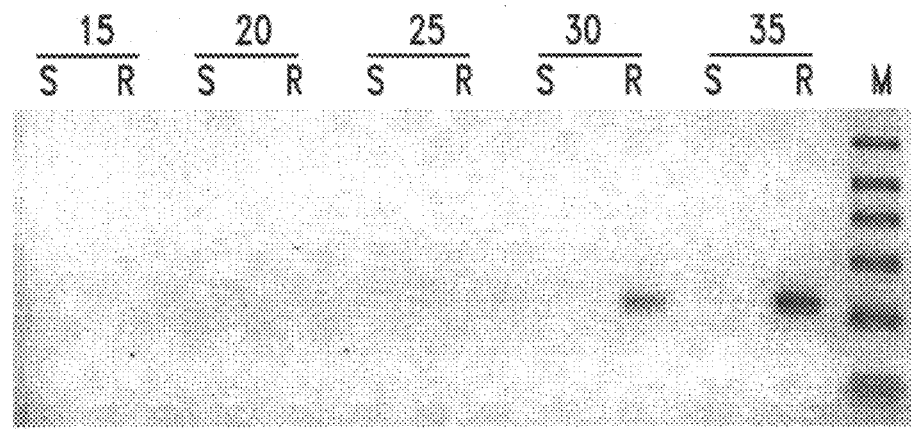

CPT-EIA was carried out using PCR amplicon prepared from a serial dilution of crude lysates of MSSA and MRSA. The results in FIG. 9 showed that CPT-EIA could detect amplicon from a 20 cycle PCR reaction starting with 100 cells or more of MRSA. The signal observed with MSSA was equivalent to background. Similar reactions analyzed by gel required PCR reactions starting with 100,000 cells to detect a band with Et-Br staining. (FIG. 10).

It was estimated that 80% of probe was cleaved with the 100 MRSA cell equivalent samples. Assuming that the efficiency of PCR is 100%, the number of molecules generated in the reaction would be 175 amol. Thus, the number of times the target is cycled in CPT is at least 50. With this amplification, it is possible to use significantly less cycles (20) than a regular PCR experiment (30 or more cycles). Using fewer cycles has two advantages. The first is that the chance of amplicon carry over is reduced, as mentioned above and second, is that the time for the PCR reaction is shortened by 1 hour. Although very rapid thermocyclers have been developed recently, most thermocyclers require approximately 3 hours for a 30 cycle PCR compared to 2 hours for 20 cycles. The total time required for PCR-CPT is under 3 hours.

The number of PCR cycles was varied between 20 and 40 using 100 MRSA or MSSA cell equivalents. CPT-EIA detected MRSA samples after 20 cycles of PCR (FIG. 11A) whereas gel agarose analysis detected sample only after 30 cycles (FIG. 11B). The theoretical difference in the number of amplicon generated in 20 versus 30 PCR cycles is 175 amol compared to 175 fmol, respectively. This corresponds to a 1000-fold difference in sensitivity, which is in agreement with the experiments described above.

It was possible to visually discriminate the presence or absence of specific target without the requirement of an instrument (data not shown). The presence of the specific target is indicated by a very light or absence of blue color due to cleavage of the probe whereas the absence of target results in a dark blue color.

In addition to its speed and reduced risk of contamination, PCR-CPT adds a second level of specificity to PCR. Indeed, CPT is based on hybridization and under the conditions used, non-specific amplicon will not be detected. This method is a step forward and may eliminate the use of Southern or nested PCR in certain applications, and use of highly specialized detection means.

CPT allows rapid and accurate detection of PCR amplicons. In addition, CPT adds a second level of amplification but without further amplifying the target, and therefore it is possible. to use significantly less number PCR cycles. This will reduce the chance of contamination and false positive. CPT adds a second level of specificity which will prevent detection of non-specific amplicons and primer-dimers. The PCR-CPT method may also be used for mismatch gene detection.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for detecting the presence of a methicillin resistant Staphylococcus in a biological sample, comprising:
   (a) treating a biological sample to expose at least one target nucleic acid molecule;
   (b) hybridizing the target nucleic acid molecule with a scissile link-containing nucleic acid probe under conditions that permit the formation of a double-stranded target-probe complex, wherein the probe consists of the nucleotide sequence AATAGAGAAA AAAAAAAAG ATGGCAAAG (SEQ ID NO:1);
   (c) reacting the target-probe complex with an enzyme, wherein the enzyme cleanses the scissile link of the target-probe complex such that at least one probe fragment is released from the complex; and (d) determining whether at least one probe fragment is released from the complex, thereby detecting the presence of a methicillin resistant Staphylococcus.

2. The method according to claim 1 wherein the step of determining whether at least one probe fragment is released from the complex comprises detecting a decrease in the amount of uncleaved probe.

3. The method according to claim 1 wherein the step of determining whether at least one probe fragment is released from the complex comprises directly detecting at least one probe fragment.

4. The method of claim 1 wherein the target nucleic acid molecule comprises a mecA gene from a Staphylococcal species.

5. The method of claim 4 wherein the target nucleic acid molecule comprises a mecA gene from a coagulase-positive Staphylococcal species.

6. The method of claim 5 wherein the target nucleic acid molecule comprises a mecA gene from *Staphylococcus aureus*.

7. The method of claim 4 wherein the target nucleic acid molecule comprises a mecA gene from a coagulase-negative Staphylococcal species.

8. The method of claim 7 wherein the target nucleic acid molecule comprises a mecA gene from *Staphylococcus epidermidis*.

9. The method of claim 1 wherein the biological sample is selected from the group consisting of a nasal swab, blood, urine, stool, abscess, and spinal fluid.

10. The method of claim 1 wherein the biological sample was first cultured in a bacteriological growth medium under conditions permitting bacterial cell growth.

11. The method according to claim 1 wherein the enzyme is RNaseH.

12. A probe for detecting the presence of a methicillin resistant Staphylococcus in a biological sample, wherein the probe consists of the nucleotide sequence AATAGAGAAA AAGAAAAAAG ATGGCAAAG (SEQ ID NO:1) and a scissile linkage.

13. A kit for detecting the presence of a methicillin resistant Staphylococcus in a biological sample, comprising:
   (a) at least one scissile link-containing nucleic acid probe, wherein the probe consists of the nucleotide sequence AATAGAGAAA AAGAAAAAAG ATGGCAAAG (SEQ ID NO:1); and
   (b) an enzyme that cleaves the scissile link when the probe is hybridized to a target nucleic acid molecule.

14. The kit according to claim 13 wherein the enzyme is RNaseH.

15. The kit according to claim 13 wherein the target nucleic acid molecule comprises a mecA gene from a Staphylococcal species.

16. The kit of claim 13 wherein the scissle link comprises ribonucleotides.

17. The kit of claim 16 wherein the probe consists of the nucleotide sequence AATAGAGaaaaAGAAAAA AGATGGCAAAG (SEQ ID NO:5); wherein upper case letters represent deoxyribonucleotides and lower case letters represent ribonucleotides.

18. The method of claim 1 wherein the target nucleic acid molecule of step (a) is amplified.

19. The method of claim 1 wherein the probe further comprises at least one detectable marker.

20. The probe according to claim 12 wherein the scissile link comprises ribonucleotides.

21. The probe of claim 20 wherein the probe consists of the nucleotide sequence AATAGAGaaaaAGAAAAA AGATGGCAAAG (SEQ ID NO:5); wherein upper case letters represent deoxyribonucleotides and lower case letters represent ribonucleotides.

22. The method of claim 1 wherein the scissile link comprises ribonucleotides.

23. The method of claim 22 wherein the probe consists of the nucleotide sequence AATAGAGaaaaAGAAAAA AGATGGCAAAG (SEQ ID NO:5); wherein upper case letters represent deoxyribonucleotides and lower case letters represent ribonucleotides.

* * * * *

UNITED STATES PATENT AND TRADEMARK OFFICE
CERTIFICATE OF CORRECTION

PATENT NO.    : 6,503,709 B1
DATED         : January 7, 2003
INVENTOR(S)   : Faouzi Bekkaoui and Lynn P. Cloney It is certified that error appears in the above-identified patent and that said Letters Patent is hereby corrected as shown below:

Column 34,
Line 61, "AATAGAGAAA AAAAAAAG ATGGCAAAG" should read
-- AATAGAGAAA AAGAAAAAAG ATGGCAAAG --
Line 64, "wherein the enzyme cleanses" should read -- wherein the enzyme cleaves --

Signed and Sealed this

Twenty-ninth Day of July, 2003

JAMES E. ROGAN
*Director of the United States Patent and Trademark Office*